United States Patent
Wong et al.

(10) Patent No.: US 8,721,923 B2
(45) Date of Patent: May 13, 2014

(54) METAL SULFIDE AND RARE-EARTH PHOSPHATE NANOSTRUCTURES AND METHODS OF MAKING SAME

(75) Inventors: Stanislaus Wong, Stony Brook, NY (US); Fen Zhang, Columbus, OH (US)

(73) Assignee: The Research Foundation for the State University of New York, Albany, NY (US)

( * ) Notice: Subject to any disclaimer, the term of this patent is extended or adjusted under 35 U.S.C. 154(b) by 186 days.

(21) Appl. No.: 12/930,914

(22) Filed: Jan. 18, 2011

(65) Prior Publication Data

US 2011/0193024 A1   Aug. 11, 2011

Related U.S. Application Data

(60) Provisional application No. 61/295,523, filed on Jan. 15, 2010.

(51) Int. Cl.
*C09K 11/08* (2006.01)
*C09K 11/70* (2006.01)

(52) U.S. Cl.
USPC .............. 252/301.4 P; 423/561.1; 423/566.1; 423/566.3; 977/773

(58) Field of Classification Search
None
See application file for complete search history.

(56) References Cited

U.S. PATENT DOCUMENTS

| | | | |
|---|---|---|---|
| 6,409,907 B1* | 6/2002 | Braun et al. | 205/317 |
| 7,235,190 B1* | 6/2007 | Wilcoxon et al. | 252/301.6 S |
| 2007/0113779 A1* | 5/2007 | Wong et al. | 117/84 |

OTHER PUBLICATIONS

Zhang, Zhen-Lei et al., "Inducing Synthesis of CdS Nanotubes by PTFE Template", Inorganic Chemistry Communications, vol. 6, pp. 1393-1394 (2003).*
Di, Xu et al., "Preparation, Characterization and Photocatalytic Activity of Flowerlike Cadmium Sulfide Nanostructure", Separation and Purification Technology, vol. 68, pp. 61-64 (2009).*
Krishnan, M. et al. "Integrated Chemical Systems: Photocatalysis at Semiconductors Incorporated into Polymer (Nafion)/Mediator Systems" Journal of the American Chemical Society, vol. 105, No. 23 (1983) pp. 7002-7003.*
Kuczynski, J. P. "Photophysical Properties of Cadmium Sulfide in Nafion Film" Journal of Physical Chemistry, vol. 88, No. 5 (1984) pp. 980-984.*

* cited by examiner

*Primary Examiner* — Kaj K Olsen
*Assistant Examiner* — Ross J Christie
(74) *Attorney, Agent, or Firm* — Hoffmann & Baron LLP

(57) ABSTRACT

The present invention provides a method of producing a crystalline metal sulfide nanostructure. The metal is a transitional metal or a Group IV metal. In the method, a porous membrane is placed between a metal precursor solution and a sulfur precursor solution. The metal cations of the metal precursor solution and sulfur ions of the sulfur precursor solution react, thereby producing a crystalline metal sulfide nanostructure.

8 Claims, 17 Drawing Sheets

METAL SULFIDE AND RARE-EARTH PHOSPHATE NANOSTRUCTURES AND METHODS OF MAKING SAME

CROSS-REFERENCE TO RELATED APPLICATION

This application claims the benefit of U.S. Provisional Application No. 61/295,523, filed Jan. 15, 2010, which is incorporated herein by reference in its entirety.

This invention was made with support by the US Department of Energy under contract number DE-AC02-98CH10886 and the National Science Foundation under CAREER award DMR-0348239. The Government has certain rights in this invention.

BACKGROUND OF THE PRESENT INVENTION

Nanomaterials, i.e. structures with at least one dimension between 1 nm and 100 nm, includes a host of substances, are fundamentally interesting due to their fascinating size-dependent optical, electronic, magnetic, thermal, mechanical, chemical, and physical properties, which are distinctive not only from their bulk counterparts but also from the atomic or molecular precursors from whence they were derived (Xia et al., *Adv. Mater.* 2003, 15, (5), 353-389; Mao et al., *Small* 2007, 3, (7), 1122-1139). In particular, semiconducting metal sulfide nanoparticulates possess novel optical and electrical properties and are considered as building blocks for photovoltaic devices including dye-sensitized cells, all-inorganic nanoparticle solar cells, and hybrid nanocrystal-polymer composite solar cells in addition to lasers and waveguides.

In recent years, high-quality semiconducting one-dimensional (1D) nanostructures, such as nanowires and nanotubes, with their inherent anisotropy, have been considered as model systems for the efficient transport of electrons and optical excitations. As such, semiconducting nanowires have been used as building blocks for a number of nanoscale energy-conversion, photonic, and electro-optical devices (including field-effect transistors, light-emitting diodes, logic gates, lasers, waveguides and solar cells), as well as electronic circuits (Sun et al., *Chem. Int. Ed.* 2008, 47, 3215-3218; Wang et al., *Science* 2001, 293, 1455). A significant amount of effort has been expended in attempting to overcome numerous challenges associated with the goal of achieving a controlled synthesis of semiconducting nanowires with reproducible morphology, crystallinity, chemical composition, and monodispersity.

Prior literature has suggested that the fabrication of PbS, CuS, and CdS nanorods can occur either by electrodeposition or injection of reactants within the channel pores of either anodic aluminum oxide or mesoporous silica templates. (Chen et al., *Surf Sci.* 2007, 601, 5142-5147; Singh et al., *Chem. Mater.* 2007, 19, 2446-2454; Routkevitch et al., *Chem. Phys.* 1996, 210, 343-352; Suh et al., *Chem. Phys. Lett.* 1997, 281, 384-388; Li et al., *Chem. Mater.* 1999, 11, 3433-3435; Xu et al., *Pure Appl. Chem.* 2000, 72, 127-135; Xu et al, *Adv. Mater.* 2000, 12, 520-522; Thiruvengadathan et al., O. *Chem. Mater.* 2005, 17, 3281-3287; Gao et al., *Adv. Mater.* 2003, 15, 739-742; Gao et al., *Nano Lett.* 2001, 1, 743-748.) As drawbacks in terms of sample quality and reaction conditions, though, nanostructures synthesized using this traditional template method are often either polycrystalline or necessitate an additional annealing step at high temperature.

It would be desirable to develop a protocol that allows for a green, cost-effective methodology of metal sulfide 1-D nanoscale synthesis without the need to sacrifice on sample quality, crystallinity, monodispersity, and purity. That is, it would be a great advance to develop a protocol aimed at metal sulfide nanowire/array formation which would overcome (i) the high-temperatures, (ii) the need for expensive equipment, (iii) the use of potentially toxic, gaseous precursors and byproducts, (iv) the utilization of costly catalysts and performance-altering capping agents (including surfactants), and/or (v) the polycrystallinity of the ultimate product, characteristic of prior art methods.

Additionally, manipulable nanoscale luminescent materials, many of which are either fluorescent, magnetic, or both, are increasingly being used for a number of significant biological applications including drug and gene delivery, biosensing, and bioimaging (De et al., *Adv. Mater.* 2008, 20, 4225-4241). However, the application of rare-earth phosphate nanostructures as biological labels for in vivo bioimaging purposes has not as yet been demonstrated.

Also, many drawbacks are associated with the synthesis of rare-earth phosphate nanostructures. For example, lanthanide phosphate ($LnPO_4$) nanorods, measuring 20-70 nm in length with aspect ratios from 2 to 7, have been synthesized by calcination of a sol-gel at 400° C. (Rajesh et al., *Microporous Mesoporous Mater.* 2008, 116, 693-697). Electrospinning has been used in conjunction with the sol-gel process as well to yield polycrystalline nanowires ranging from 60 to 300 nm, after calcination at 650 to 750° C. (Hou et al., *Chem. Mater.* 2008, 20, 6686-6696; Xu et al., *J. Phys. Chem. C* 2009, 113, 9609-9615). Generally, the hydrothermal methodology has been primarily used for the synthesis of 1D $LnPO_4$ nanostructures, measuring typically 20-60 nm in diameter with lengths from several hundred nm to several microns. The treatment usually involves reaction in a Teflon-lined stainless-steel autoclave often under anomalous pH conditions, at a relatively high temperature (in the range of 150-240° C.), and involving a reaction times ranging from a few hours up to several days, depending on the experimental circumstances (Chen et al., *J. Phys. Chem. C* 2008, 112, 20217-20221; Fang et al., *Cryst. Growth Des.* 2005, 5, 1221-1225; Cao et al., *Nanotechnology* 2005, 16, 282-286, Yu et al., *Mater. Lett.* 2007, 61, 4374-4376; Lam et al.; *J. Cryst. Growth* 2007, 306, 129-134; Yan et al., *Chem.—Eur. J.* 2005, 11, 2183-2195; Chen et al., *J Phys. Chem. C* 2008, 112, 16818-16823; Zheng et al., *J. Cryst. Growth* 2005, 280, 569-574; Fang et al., *J. Am. Chem. Soc.* 2003, 125, 16025-16034; Yan et al., *Solid State Commun.* 2004, 130, 125-129; Yu et al., *J. Phys. Chem. B* 2004, 108, 16697-16702). The synthesis of well-defined crystalline $CePO_4$ nanowires with a diameter of 3.7 nm was reported by use of a microemulsion reaction medium, but could take as long as a month to produce, while ultrasound irradiation of an inorganic salt aqueous solution has been reported for the synthesis of $CePO_4$: Tb and $CePO_4$: Tb/$LaPO_4$ core/shell nanorods (Xing et al., *J. Phys. Chem. B* 2006, 110, 1111-1113; Zhu et al., *Nanotechnology* 2006, 17, 4217-4222).

Hence, there is a need for a more facile, milder, less technically demanding, but more cost-effective approach towards the generation of sulfide and phosphate nanostructures.

SUMMARY OF THE PRESENT INVENTION

In one embodiment, the present invention is a method of producing a crystalline metal sulfide nanostructure. The method comprises providing a metal precursor solution and providing a sulfur precursor solution; placing a porous membrane between the metal precursor solution and the sulfur precursor solution, wherein metal cations of the metal precursor solution and sulfur ions of the sulfur precursor solution react, thereby producing a crystalline metal sulfide nanostructure, wherein the metal is a transitional metal or a Group IV metal. Examples of the metal include copper, lead, cadmium, iron, manganese, cobalt, nickel, zinc, magnesium, tin, germanium, or mixtures thereof. Preferably, the metal sulfide nanostructure is single crystalline.

In one embodiment, the metal cations and sulfide ions predominantly nucleate to form metal sulfides within the confines of the pores. In another embodiment, the metal cations and sulfide ions predominantly nucleate at the walls of the pores.

In one embodiment, the metal precursor solution is a cadmium solution, and the method takes places at about 70° C. to about 85° C., wherein the nanostructure produced is cactus-like nanostructures.

In another embodiment, the present invention is a method of producing a crystalline rare earth phosphate nanostructure. The method comprises providing a rare earth metal precursor solution and providing a phosphate precursor solution; placing a porous membrane between the rare earth metal precursor solution and the phosphate precursor solution, wherein metal cations of the rare earth precursor solution and phosphate ions of the phosphate precursor solution react, thereby producing a crystalline rare earth phosphate nanostructure. Examples of the rare earth metal include cerium, lanthanum, terbium and samarium, or mixtures thereof. Preferably, the method further comprises doping the rare earth metal precursor solution with a different rare earth metal. For example, the rare earth phosphate nanostructure is cerium phosphate and doped with terbium. Preferably, he rare earth phosphate nanostructure is single crystalline.

In another embodiment, the present invention is a biological label comprising: a single crystalline 1D rare earth metal phosphate nanostructure wherein the biological label exhibits photoluminescence. For example, the biological label is a single crystalline 1D rare earth metal phosphate nanostructure is $CePO_4$, preferably doped with Tb.

In one embodiment, the present invention is a crystalline nanostructure comprising $CePO_4$ in a sheaf-like bundle formation.

The present invention overcomes the drawbacks in the prior art by providing preparation of (a) discrete, individual motifs and (b) arrays of crystalline and pure semiconducting metal sulfide nanowires, synthesized via an inexpensive, generalizable, simplistic, and ambient modified template technique.

Additionally, the present invention overcomes the drawbacks in the prior art by providing a facile, room-temperature template-directed synthetic route towards the production of distinctive morphologies: (a) high-purity, high-aspect-ratio, single-crystalline ultrathin nanowires (external to the template), as well as (b) sheaf-like nanowire bundles (within the template pores) of Rare-Earth phosphates at room temperature. The ultrathin nanowires are easily fabricated on a reasonably large scale, i.e. >500 mg per lab run, which has been previously been difficult to achieve using a template-mediated synthesis. Moreover, the present invention provides the use of these as-prepared Rare-Earth phosphate ultrathin nanowires as fluorescent labels for non-toxic in vivo bioimaging.

DETAILED DESCRIPTION OF THE PRESENT INVENTION

Figure 1A:
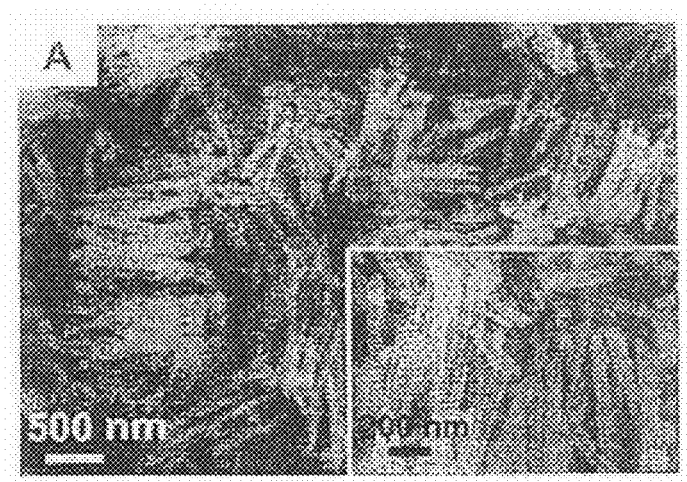
FIG. 1A. Typical SEM image of as-prepared CdS cactus-like nanostructures, prepared using polycarbonate membranes with 100-nm pore diameters at 80° C. Associated inset shows a correspondingly magnified view of as-generated products.

The present invention relates to the field of nanotechnology, including nanostructures and their applications.

Crystalline Nanostructures

The present invention includes metal sulfide single crystalline nanostructures and rare-earth phosphate single crystalline nanostructures. These nanostructures include free-standing one dimensional nanostructures and include nanoarrays comprising a plurality of such nanostructures. The invention also includes methods of making such nanostructures. In particular, the methods enable the making of nanostructures with predictable size and morphology. The methods comprise the use of template membranes and can proceed at room temperature.

The nanostructures of the invention are single crystalline or polycrystalline. Typically, the nanostructures are at least 80% free, preferably at least 95% free, more preferably at least 99% free, and most preferably virtually completely free of defects and/or dislocations. As defined in this specification, defects are irregularities in the crystal lattice (i.e., intrinsic defects). Some examples of defects include a non-alignment of crystallites, an orientational disorder (e.g., of molecules or ions), vacant sites with the migrated atom at the surface (Schottky defect), vacant sites with an interstitial atom (Frenkel defects), point defects, grain boundary defects, and non-stoichiometry of the crystal. An example of a dislocation is a line defect in a crystal lattice.

Additionally, the nanostructures are preferably at least 95% free, more preferably at least 99% free, and most preferably virtually completely free of amorphous materials and/or impurities. Examples of amorphous materials include organic surfactant molecular groups, such as bis(2-ethylhexyl)sulphosuccinate, undecylic acid, sodium dodecyl sulfate (SDS), Triton X-100, decylamine, or double-hydrophilic block copolymers, which are present on the surfaces of prior art nanostructures. Examples of impurities include an element different from the elements of the crystalline structure and a vacancy.

The nanostructures of the invention include one-dimensional nanostructures, such as nanotubes, nanowires, and nanorods. Nanotubes are hollow with varying wall thicknesses. Nanowires and nanorods are solid. Nanowires and nanorods differ in aspect ratios (i.e., diameter/length). An aspect ratio of greater than 5 is known as a nanowire. Nanorods typically have an aspect ratio of about 3 to about 5. The diameter of the one-dimensional nanostructure typically ranges from about 1 to about 10,000 nm, more typically from about 2 nm to about 2 µm. The length of the nanostructure typically ranges from about 20 nm to about 20 µm, more typically about 10 µm.

The present invention includes a nanoarray comprising a plurality of crystalline one-dimensional nanostructures of the invention. Preferably, a nanoarray is at least 50%, 60%, 70%, 80%, 90%, 95%, 99% or virtually completely monodisperse.

In one embodiment, the crystalline nanostructures comprise hexagonal würtzite cactus-like metal sulfide nanostructures. In another embodiment, the crystalline nanostructure comprises rare earth phosphates in a sheaf-like bundle formation.

Metal Sulfide Nanostructures

In one embodiment of the present invention, the nanostructures have the chemical formula of XS. X represents metallic elements with the oxidation state of +2.

X can be a transitional metal, or a Group IV metal. X can be, for example, copper (Cu), lead (Pb), cadmium (Cd), iron (Fe), manganese (Mn), cobalt (Co), nickel (Ni), zinc (Zn), magnesium (Mg), tin (Sn), germanium (Ge), silver (Ag), mercury (Hg), Tl (thallium) or mixtures thereof. An example of a mixture is $Fe_{1-x}Co_x$, wherein x is $0 < x < 1$.

Specific examples of XS compounds include, but are not limited to, CuS, PbS, and CdS. The crystalline nanostructures include crystalline hexagonal-phase CuS, cubic-phase PbS, cubic-phase CdS and hexagonal würtzite CdS.

In the methods of making nanostructures with the formula XS, any compound comprising X can be used as precursor, hereinafter termed "X-precursor." These precursors are soluble in aqueous solvents.

Examples of X-Precursors Include:

Cu (copper): nitrate ($Cu(NO_3)_2$), acetate ($Cu(CH_3CO_2)_2$); halides, such as bromide ($CuBr_2$), chloride ($CuCl_2$), and iodide ($CuI_2$); etc.

Pb (lead): acetate; halides, such as, bromide, chloride, and iodide; nitrate, etc.

Cd (cadmium): acetate; halides, such as, bromide, chloride, and iodide; nitrate, etc.

Zn (zinc): acetate $Zn(CH_3CO_2)_2$; halides, such as bromide ($ZnBr_2$), chloride ($ZnCl_2$), fluoride ($ZnF_2$), and iodide ($ZnI_2$); lactate $Zn[CH_3CH(OH)CO_2]_2$; nitrate ($Zn(NO_3)_2$); oxalate ($ZnC_2O_4$); perchlorate ($Zn(ClO_4)_2$); sulfate ($ZnSO_4$); etc.

Fe (iron): acetate ($Fe(CH_3CO_2)_2$); halides, such as bromide ($FeBr_2$), chloride ($FeCl_2$), and iodide ($FeI_2$); nitrate ($Fe(NO_3)_2$), etc.

Mn (manganese): acetate ($Mn(CH_3CO_2)_2$); halides, such as bromide ($MnBr_2$), chloride ($MnCl_2$), and iodide ($MnI_2$); nitrate ($Mn(NO_3)_2$), etc.

Co (cobalt): acetate ($Co(CH_3CO_2)_2$); halides, such as bromide ($CoBr_2$), chloride ($CoCl_2$), and iodide ($CoI_2$); nitrate ($Co(NO_3)_2$), etc.

Ni (nickel): acetate ($Ni(CH_3CO_2)_2$); halides, such as bromide ($NiBr_2$), chloride ($NiCl_2$), and iodide ($NiI_2$); nitrate ($Ni(NO_3)_2$), etc.

Sn (tin): acetate; halides, such as, bromide, chloride, and iodide; nitrate, etc.

Ge (germanium): acetate; halides, such as, bromide, chloride, and iodide; nitrate, etc.

Ag (silver): acetate; halides, such as, bromide, chloride, and iodide; nitrate, etc.

Hg (mercury): sulfate, etc.

Tl (thallium): acetate; sulfate, carbonate, halides, such as, bromide, chloride, and iodide; nitrate, etc.

Two or more X-precursors can be used to make a mixed X-precursor. For example, a mixed X-precursor can comprise iron chloride and cobalt chloride, which can form nanostructures of the formula $(Fe_{1-x}Co_x)Cl_2$, wherein x is $0 < x < 1$.

In these methods, any compound comprising sulfur can be used as a precursor, termed herein as an "S-precursor." These precursors are soluble in aqueous solvents.

Examples include $Na_2S$, $Li_2S$, $K_2S$, $Rb_2S$, $Cs_2S$, $Fr_2S$, $(NH_4)_2S$, MgS, BeS, CaS, SrS, BaS, RaS and aqueous $H_2S$.

Different ions form in the metal precursor solution and the sulfur precursor solution, e.g., $X^{2+}$; $S^{2-}$.

The methods can further comprise doping of the nanostructures with elements such as, for example, lanthanides and other metal ions. In such embodiment, doping compounds are added to the X precursor solution.

Rare-Earth Phosphate Nanostructures

In one embodiment of the present invention, the nanostructures have the chemical formula of $Re(PO_4)$. Re is selected from the lanthanide series. The lanthanide series includes La, Ce, Pr, Nd, Pm, Sm, Eu, Gd, Tb, Dy, Ho, Er, Tm, Yb and Lu.

Specific examples of $Re(PO_4)$ compounds include, but are not limited to, $Ce(PO_4)$, $LaPO_4$, $TbPO_4$, and $SmPO_4$. The crystalline nanostructures include crystalline hexagonal-phase $Ce(PO_4)$.

In the methods of making nanostructures with the formula $Re(PO_4)$, any compound comprising Re can be used as a "Re-precursor," hereinafter termed "Re-precursor." These precursors are soluble in aqueous solvents. Preferred examples of Re-precursors include nitrates and halides (such as chlorides and bromides) of the lanthanides, and their mixtures, for example, $CeCl_3$, $Nd(NO_3)_3$, $Nd(OAc)_3$, $Er(NO_3)_3$, $Ho(NO_3)_3$, etc.

Two or more Re-precursors can be used to make a mixed Re-precursor. Examples include $La_xTb_{1-x}$ and $(Ce_{1-x}Tb_x)Cl_3$, wherein x is $0<x<1$.

In these methods, any compound comprising phosphate can be used as a precursor, termed herein as a "Phos-precursor." These precursors are soluble in aqueous solvents. Examples include $NaH_2PO_4$, $KH_2PO_4$, and $LiH_2PO_4$.

A Re-precursor and Phos-precursor are each placed into separate aqueous solvents to form precursor solutions. Accordingly, different ions form in each solution, e.g., $Ce^{3+}$; $PO_4^{3-}$. The yield of $Re(PO_4)$ nanostructures, typically of nanowires, is about 60% to about 70%, more typically about 65%.

In a preferred embodiment, the Re-precursor solution is doped with a D-precursor. D is any element in the lanthanide series. Preferred examples of D-precursors include nitrates and halides (such as chlorides and bromides) of the lanthanides, and their mixtures, for example, $TbCl_3$, $Tb(NO_3)_3$, $Nd(OAc)_3$, $Er(NO_3)_3$, $Ho(NO_3)_3$, etc. The resulting nanostructure can be designated as $Re(PO_4)$:D. A preferred example is $Ce(PO_4)$:Tb. Doping can improve the photoluminescent performance of the resulting nanostructures.

Methods of Making the Nanostructures

The concentrations of the two selected precursor solutions range from being equivalent (i.e., equimolar) to where one solution is ten times as concentrated as the other, more typically, twice or thrice as concentrated as the other.

Typically, precursors are used by themselves. In some embodiments, additional solvents can be used to accelerate reactivity. Examples of suitable aqueous solvents include water; alkyl and alkylene glycols, such as, for example, ethylene glycol; mixtures of water and alcohols (methanol, ethanol, isopropanol, butanol, pentanol, hexanol); mixtures of water and acids, such as, for example, acetic acid, sulfuric acid, phosphoric acid, propionic acid, ethanoic acid, and/or nitric acid; and mixtures of ethylene glycol and acids, such as, for example, citric acid and/or tartaric acid. Solvents are selected according to the particular precursors used as would be known to a skilled artisan.

The two selected precursor solutions are then placed in contact with each other in a manner which allows production of single crystals. Reactions can be run at any temperature that is between the melting and boiling points of the solvents. Preferably, the reaction is run at room temperature to about 80° C. The precursor solutions are placed into contact with each other at a slow rate. Preferably, the precursor solutions are placed into two reservoirs separated from each other by a template membrane.

An example of a set-up which allows for such a slow rate of contact of precursor solutions is a double-diffusion set-up. In this set-up, a different precursor solution is placed into either half of a U-tube cell separated by a template membrane. For the growth of XS nanostructures, an X-precursor solution is on one side and an S-precursor solution is on the other side. For the growth of XS nanostructures, an X-precursor solution is on one side and an S-precursor solution is on the other side. For the growth of $Re(PO_4)$ nanostructures, a Re-precursor solution is on one side and a Phos-precursor solution is on the other side.

A double diffusion crystallization set-up process is described in Park et al., *Adv. Mater.*, 2002, 14:1167; Park et al., *J. Mater. Chem.*, 2004, 14:2291; and Peters et al., *J. Chem. Soc., Dalton Trans.*, 2001, 24:358, all of which is incorporated herein by reference.

The precursor solutions flow into the membrane pores. The membrane slows down the rate of contact of the ions of the precursor. When the two ions meet, crystallization occurs thereby forming nanostructures within the membrane pores. The nucleation and growth of crystalline nanostructures occur essentially instantaneously through the direct chemical interaction between ions of the two different precursor solutions.

Although not wanting to be limited by a mechanism, it is believed that the formation mechanism of nanostructures of the present invention is analogous to a biomimetic crystallization process (Dorozhkin et al., *Cryst. Growth Des.*, 2004, 4, 389). That is, the growth of nanostructures within the confinement of a template membrane is analogous to the precipitation of single crystals of calcium carbonate and calcium phosphate within the confinement offered by gels, micelles, chitin scaffolds, and collagen matrices. The interactions between the precursor molecules are likely stronger than those between the precursor molecules and the pore walls. The nucleation rate is primarily dictated by the supersaturation of the solution.

Single crystals of nanoscale materials derive from isolated, disparate nucleation sites (consisting of XS nuclei or $Re(PO_4)$ nuclei generated via the reaction between their respective ions), which then grow by extension through the porous network. Continued growth then occurs at the crystal surface at a rate limited by ion availability, until the crystal impinges on the template surface, which ultimately limits further growth.

The precursor are in contact until the desired growth is achieved, e.g., from about 1 h to about 100 hrs, more typically from about 2 hrs to about 24 hrs, even more typically from about 5 hrs to about 12 hrs. The membrane is then removed.

In the methods of making free-standing one-dimensional nanostructures, the membranes can be removed from the resultant nanostructures by immersion in a solution as would be known by a skilled artisan. For example, the membranes can be removed by immersion in methylene chloride at room temperature, and preferably, with sonication. Thereafter, to retrieve free-standing nanostructures, the base solution is diluted in several steps with distilled water and an organic solvent. Free-standing nanostructures are then collected by centrifugation or filtration, as would be known by a skilled artisan.

In the methods of making nanoarrays, a membrane containing a nanoarray is attached to a substrate to form a composite, as would be known by a skilled artisan. The nanoarray can be attached, for example, by glue, or by vacuum or sputtering coating one side of the membrane containing nanostructures with a thin film of substrates. An example of a glue is Epoxy resin. Examples of substrates include a paper towel, gold, polymeric thin films graphite, mica, silica, silicon, wood, glass, alumina, metal, and metal oxide.

The resulting composite is immersed into an aqueous base solution (e.g., NaOH aqueous solution) until the membrane is dissolved (e.g., for about 15 minutes to about 2 hrs). A nanoarray protruding out from the surface of the substrate is obtained. Preferably, the nanoarray is washed with distilled, deionized water and air-dried.

The methods of the present invention do not require that the resultant nanostructures be annealed. The method avoids use of pyrophoric, fammable or unstable precursors, and avoids the use of organic solvents.

Methods of Controlling the Dimensions and Morphology of Nanostructures

The morphology of the resulting nanostructures can be predictably controlled by varying one or more different parameters of the methods of the invention.

For example, the temperature used during preparation of certain species of the nanostructures influences the morphological motif and/or crystallographic structure of the resultant nanostructures. For instance, as the temperature increases, needle-like ultrathin structures measuring a few nanometers in length form on the surfaces of the XS nanostructures (e.g., on the CdS nanostructures). Such nanostructures are herein termed "cactus-like nanostructures." For example, at a temperature of higher than room temperature such needle-like ultrathin structures start to form, more typically from about 70° C. to about 80° C.

Additionally, the pH of the reaction can influence the morphology of the resulting nanostructures. For example, hexagonal-phase $Re(PO_4)$ nanostructures are obtained when the pH is acidic.

Additionally, the dimensions and morphology of the resultant nanostructures are controlled by the structure of the template membranes within which the nanostructures are grown. The membranes act to spatially direct crystal growth.

The pore sizes of the template membranes are varied according to the desired dimensions and characteristics of the resultant nanostructures. For example, the diameters of the pores can range from about 1 nm to about 100 μm, typically from about 3 nm to about 2 μm, more typically from about 20 nm to several hundred nanometers. Some examples of pore diameters include about 10, 25, 50, 60 80, 100, 150, 200, 300 and 500 nanometers.

As the pore size increases to a certain maximum level, one-dimensional nanostructures become straighter and smoother with fewer extraneous particulate debris. The resultant nanostructures typically have diameters which are approximately 20 to 80% larger (or smaller) than the reported pore size of the membrane. For example, using a membrane with about 100 nm diameter pores produces one-dimensional nanostructures having outer diameters in the range of about 85 to about 115 nm. The diameters of $Re(PO_4)$ nanowires are typically smaller than the diameters of the pores, for example about 20% to about 70% smaller than the diameter of the pores. The lengths of the one-dimensional nanostructures range from several microns to the entire length of the template membranes. Typically, the diameter is uniform throughout the length of a nanorod.

The template membranes can have varying pore densities. For example, a membrane can have one single pore to about $10^9$ pores/cm$^2$ or to about $10^{11}$ pores/cm$^2$. A membrane can have pores of uniform size or can have pores of varying sizes.

The thicknesses of the membranes are varied according to the desired lengths of the nanostructures. Membranes typically range from approximately about 20 nm to about 20 μm, more typically from about one to about fifteen microns, in thickness. For XS, the maximum length of a nanostructure is typically limited by the thickness of a membrane. For $Re(PO_4)$, the lengths of nanostructures is typically up to about 85% longer than the thickness of the membranes.

The width of an array corresponds with the width of the membrane on which the array was grown. The length of an array corresponds with the thickness of the membrane. The nanostructures of an array can be monodisperse by using a membrane with uniform pores. Alternatively, the nanostructures of an array can be polydisperse by using a membrane with a variety of different pore sizes.

Additionally, the distances between each individual nanostructure within an array is controlled by varying the pore densities on the membranes. All other parameters being equal, the more dense the porosity of a membrane, the closer each individual nanostructure is to each other. Alternatively, the pores on the membrane can be placed in such a fashion that they are not at a uniform distance from each other.

Although, within a nanoarray, the one-dimensional nanostructures are individually separated from each other, they form a dense, continuous network. Preferably, the nanostructures are roughly parallel to each other and vertically oriented on the substrates to form a packed array, stretching over micron-sized areas.

The shapes of the XS nanostructures reflect the morphology and inner surface roughness of the pores within which they are grown. That is, the morphology of the XS nanostructures can spatially map out the interior nanoscopic profile and localized contours of the internal pores of the membranes.

For example, if the inner surface of a pore within which a XS nanostructure is grown is smooth, then the resultant XS nanostructure is straight and smooth. Alternatively, if the inner surface of a pore is rough, then the resultant XS nanostructure has protrusions and/or depressions on its surface.

In one embodiment, the membranes used in the methods can be made from any suitable polymer. Preferred membranes include "track-etch" polymeric membranes. These commercially available membranes are usually prepared from either polycarbonate or polyester.

Polycarbonates are polymers having functional groups linked together by carbonate groups (—O—(C=O)—O—) in a long molecular chain. Polycarbonate membranes are produced by heavy ion irradiation of a polycarbonate material and then chemical etching of the latent ion tracks. See, for example, Yu et al., Journal of Membrane Science, 2006, 282, 393-400. By varying the etching conditions, different pore sizes of the polycarbonate membranes can be produced. Additionally, different pore geometries can be produced, for example, as circular and oval shapes In another embodiment, porous alumina membranes are used as template membranes. Alumina membranes have pores which are tunable in the range of 4 to several hundred nanometers. Pore densities as high as $10^{11}$ pores/cm$^2$ can be obtained, and typical membrane thicknesses can range from 10 to 100 μm. An example of an alumina membrane is porous anodic alumina (AAO) membrane.

The type of template membrane used strongly influences whether nanotubes or nanowires/nanorods are produced. For example, depending on the template membrane used, the nucleation of metal hydroxides can be in either a predominantly homogenous fashion or a predominantly heterogeneous fashion.

In a homogeneous nucleation, nucleation predominantly first occurs within the solution without attachment to a foreign body. Such nucleation tends to occur if the interactions between precursor molecules are stronger than those between the precursor molecules and the pore walls. In particular, the nucleation process and accompanying product formation happen within the voluminous confines of the pores themselves in a homogeneous-type process. That is, single crystals of nanoscale metal sulfides and RE phosphates derive from isolated, disparate nucleation sites, which then grow by extension throughout the porous network. In this specification, the confines of a pore are defined as anywhere inside a pore excluding the wall of the pore. Continued growth then occurs at the particle surface at a rate limited by ion availability, until the crystal impinges on the template surface itself, which ultimately limits further particle growth. Within the confines of the template pores, as-formed particles in this embodiment essentially self-assemble with each other into either wire-like or rod-like motifs.

In a heterogeneous nucleation, nucleation predominately first occurs by attachment to a foreign body; in this case, the foreign body is the pore inner wall. Such nucleation tends to occur if the interactions between the precursor molecules are weaker than those between the precursor molecules and the pore walls. The nucleation and accompanying growth processes may tend to be localized at the surfaces of the pore walls in a heterogeneous-type process.

Such a heterogeneous process occurs, for instance, if the pore wall is positively charged while the precursor particles are negatively charged. This preferential confinement of growth to the inherent geometry of the pore walls can therefore lead to the generation of primarily tube-like motifs upon the elongation and assembly of the as-formed particles. Such a process has been previously noted in the case of polymeric microtubules formed in templates, wherein nascent polymer chains initially adsorbed to the pore walls yielding a thin polymer "skin" that became thicker with time until it was quenched with water (Martin et al., *J. Am. Chem. Soc.* 1990, 112, 8976-8977).

With continued reaction, there is a lateral thickening of the tubular structure. At a certain point of the reaction, the further supply of precursors to the inside is blocked by the ever-growing tube thickness coupled with an ever-decreasing inner tube diameter. If the reaction is continued further, the entire porous interior of the template is filled completely. In other words, continued growth of the nanotubes is limited only by precursor ion availability and diffusivity as well as by intrinsic geometrical constraints imposed by the template channels. Hence, nanowires/nanorods are considered as the ultimate limit of nanotube growth in terms of its width. This nanotube-to-solid nanowire/nanorod transformative mechanism has been previously proposed with respect to the synthesis of $TiO_2$ nanotubes and nanowires within alumina (AAO) templates (Cochran et al., *Acta Mater.* 2007, 55, 3007-3014).

Polycarbonate membranes typically encourage a homogeneous-type nucleation. For example, nanowires/nanorods are formed by use of polycarbonate membranes. Alumina membranes typically encourage a heterogeneous-type nucleation. For example, nanotubes are formed by AAO membranes.

Additionally, membranes can be chemically modified to convert a homogenous-type membrane to a heterogeneous-type membrane, and visa-versa, by changing the polarity of the wall. In particular, if a pore wall having a certain polarity produces nanotubes, then transformation of a polar wall into a nonpolar wall, or transformation of a nonpolar wall into a polar wall, will produce nanowires/nanorods. A surfactant can be used to change the surface charge on the pore walls of a membrane. Additionally, the walls can be modified by a chemical reaction between introduced chemical ligands and existing functional groups on the walls (such as, for example, hydroxy groups).

Varying the conditions of the synthesis also affects the dimensions and characteristics of the resultant nanostructures. For example, as the duration of the synthesis increases, a greater portion of each pore is filled with the precursors. If the desired resultant nanostructures are nanotubes, then the duration of deposition is stopped before the precursors are allowed to fill the entire pore volume. The thickness of the walls of the nanotubes increases as the duration of deposition increases. If the desired resultant nanostructures are nanowires/nanorods, then the duration of deposition is allowed to proceed until the precursors fill the whole pore volume. The precursors are in contact until the desired growth is achieved, e.g., from about 30 minutes to about 100 hrs, more typically from about 1 hr to about 6 hrs.

Additionally, the pH concentration and synthesis temperature also govern the morphologies of the resulting nanotubes and nanowires/nanorods. Lower pH and lower temperatures favor the production of short, nanotubes. With sulfides, a lower pH promotes particle nucleation. Higher temperatures favor the growth of longer, thicker wires. In particular, a higher temperature accelerates ion diffusion rates across template membranes.

For example, during a homogeneous type formation process, a higher temperature promotes high diffusion rates and correspondingly high local concentrations of interacting precursor ions. These conditions therefore lead to initial particle formation followed by subsequent aggregation, coalescence, and self-assembly of these constituent particles to yield solely solid nanostructures. Upon reduction of temperature, shorter solid nanostructures (a few micrometers in length versus tens of micrometers in length) are obtained and, in some cases, isolated particles are also generated in addition to the wire-like motifs. Simultaneous decreases in both temperature and base concentration typically yield only small, discrete particles, measuring tens of nanometers.

EXAMPLES

Sulfide Nanostructures

The preparation and characterization of (a) discrete, individual motifs and (b) arrays of crystalline and pure semiconducting metal sulfide (CuS, PbS, and CdS) nanowires, synthesized via an inexpensive, generalizable, simplistic, and ambient modified template technique are shown here. Control has been demonstrated over the diameters and lengths of one-dimensional (1-D) nanostructures through corresponding variations in the template membrane's pore size and thickness. Not only have cubic-phase 1-D CdS nanowires been successfully generated but also produced, at slightly elevated temperatures, unusual CdS cactus-like, hierarchical nanostructures, consisting of tiny nano-needles projecting out from the outer surfaces of parent CdS nanotube motifs. Vibrational properties of all of these metal sulfide nanomaterials have been extensively studied. In addition, the results indicate that the as-prepared hexagonal-phase CdS cactus-like nanotubes evinced a higher photocatalytic degradation activity than that of both cubic CdS nanowires and their commercial bulk counterparts.

Experimental Section

Synthesis. Polycarbonate track-etch membranes of ca. 6 μm in thickness, containing pore sizes of 50, 100 and 200 nm diameter, respectively, were purchased from Whatman Co., UK. The membranes were initially hydrated by immersion and sonication in a small volume of distilled, deionized water for a few minutes, so as to limit the formation of air bubbles either within their interior pore channels or on the membrane surfaces. In order to avoid unwanted particle formation and deposition onto the external surfaces of the polycarbonate (PC) membranes, microcontact printed OTS-SAMs (octadecyltetrachloro-silane self-assembled monolayers) were used as passivation layers (Kumar et al., *Appl. Phys. Lett.* 1993, 63, 2002-2004). Hence, a homemade PDMS (polydimethylsiloxane) stamp was initially inked with a 10 mM hexane solution of OTS and dried with nitrogen. The stamp was then placed into contact with the PC membranes for 30 seconds and then peeled off carefully.

Subsequently, the membrane was mounted between two half arms of a U-shaped tube. Precursors $Na_2S$ (Alfa Aesar, 98%), $Cu(NO_3)_3$ (Alfa Aesar, 98%), $Pb(CH_3COO)_2$ (Aldrich, 99.99%), and $Cd(NO_3)_2$ (Alfa Aesar, 98.5%) were of analytical grade and were used without further purification. In a typical synthesis, one of the two half-cells was filled with freshly prepared 0.01 M $Na_2S$ solution, which was adjusted to pH=6 using HCl. The other half-cell contained a 0.01 M solution of either Cu(NO$_3$)$_2$, Pb(CH$_3$COO)$_2$, or Cd(NO$_3$)$_2$, used to generate either CuS, PbS, or CdS nanowires, respectively. The system was then left unperturbed for an incubation period of as little as 5 h and up to 12 h at temperatures ranging from ambient conditions to 80° C. In the specific cases of PbS and CuS, such temporal and thermal variations did not appreciably affect either the morphology or the composition of the resultant products. By contrast, an increase in reaction temperature to 80° C. resulted in the transformation of cubic zinc blende CdS nanowires into hexagonal würtzite cactus-like CdS nanostructures.

Subsequent to precursor solution immersion and product formation, either a black color (CuS and PbS) or a yellow hue (CdS) was observed, associated with the polycarbonate membrane, which was then detached, sonicated for ~2 min to remove unwanted particles on the surface, and thoroughly washed with distilled water, prior to dissolution and removal with methylene chloride. As-prepared sulfide nanowires were then collected and isolated from solution by centrifugation after washing.

Characterization. As-prepared samples were thoroughly characterized using a number of different methodologies, including powder X-ray diffraction (XRD), field-emission scanning electron microscopy (FE-SEM), transmission electron microscopy (TEM), high resolution TEM (HRTEM), selected area electron diffraction (SAED), and energy-dispersive X-ray spectroscopy (EDX), as well as with Raman, UV-visible, and photoluminescence (PL) spectroscopies.

X-ray Diffraction. Crystallographic and purity information on as-prepared sulfide nanowires were initially obtained using powder X-ray diffraction (XRD). To prepare analyzable samples, the resulting sulfide nanowires were rendered into slurries in ethanol, sonicated for ~1 min, and then air-dried upon deposition onto glass slides. Diffraction patterns were collected using a Scintag diffractometer, operating in the Bragg configuration using Cu K$\alpha$ radiation ($\lambda$=1.54 Å) from 10 to 80° at a scanning rate of 2° per minute.

Electron Microscopy. The morphology and size of the resulting sulfide nanowires were initially characterized using a field emission SEM (FE-SEM Leo 1550) at accelerating voltages of 15 kV, which was equipped with EDS capabilities. Specifically, samples for SEM were prepared by dispersing as-prepared sulfide nanowires in ethanol, sonicating for ~2 min, and then depositing these nanostructures onto a silicon wafer, attached to a SEM brass stub using conductive carbon tape. All of these samples were subsequently conductively coated with gold by sputtering for 15 s, so as to minimize charging effects under SEM imaging conditions.

Low-magnification TEM images were taken at an accelerating voltage of 80 kV on a FEI Tecnai12 BioTwinG$^2$ instrument, equipped with an AMT XR-60 CCD Digital Camera System. High-resolution TEM (HRTEM) images and SAED patterns were obtained on a JEOL 2010F instrument at accelerating voltages of 200 kV. Specimens for all of these TEM experiments were prepared by sonicating the as-prepared product for 2 min in ethanol to ensure adequate dispersion of the nanowires, and placing one drop of the solution onto a 300 mesh Cu grid, coated with a lacey carbon film.

Optical Spectroscopy. Raman spectra were obtained on solid samples dispersed in ethanol and placed onto a Si wafer. Spectra were obtained on a Renishaw 1000 Raman microspectrometer with excitation from argon ion (514.5 nm), He—Ne (632.8 nm), and diode (780 nm) lasers, respectively, at a power level of 5 mW. In addition, a Renishaw System 1000 microscope with a tunable argon ion laser was used to acquire Raman data at 488 nm excitation. A 50× objective and low laser power density were used for the irradiation of the sample and for signal collection. The laser power was kept sufficiently low to avoid heating of the samples by optical filtering and/or defocusing of the laser beam at the sample surface. Spectra were collected in the range of 3000-100 cm$^{-1}$ with a resolution of 1 cm$^{-1}$.

UV-visible spectra were collected at high resolution with a Thermospectronics UV1 spectrometer using quartz cells with a 10-mm path length. Spectra were obtained for as-prepared sulfide nanorods, which were previously sonicated in distilled water so as to yield homogeneous dispersions. UV-visible absorption spectra were recorded using distilled water as a blank.

Samples for PL spectra were dispersed in deionized water and sonicated for 1 min. Fluorescence data were obtained at room temperature on a Jobin Yvon Spex FluoroMax-4 instrument with a 10 s integration time. PL spectra for CuS, PbS, and CdS nanostructures were measured at excitation wavelengths of 370, 495, and 400 nm, respectively, in accordance with the literature.

Photocatalytic Degradation Activity.

In a typical experiment, CdS powdered catalyst (with a resulting concentration of 0.5 g/L), suspended in an aqueous solution of either 50 ppm Rhodamine B or methyl orange, was ultrasonicated for 10 min and magnetically stirred under dark, unilluminated conditions for 30 min so as to establish an adsorption-desorption equilibrium with respect to the individual dye species. After given irradiation time intervals with UV light at 366 nm at a 5 cm separation distance, the photocatalytic performance of the various CdS nanoscale catalysts was subsequently gauged by measuring changes in the intensity of the optical absorbance peaks, localized at either 555 nm or 464 nm, of the aqueous supernatant aliquots containing either Rhodamine B or methyl orange dye species, respectively. Analogous control experiments were performed either without CdS (blank) or in the presence of a commercial bulk sample (CERAC Inc.; particle size corresponding to −325 mesh or <64 µm), normalized for identical metal sulfide concentrations.

Results and Discussion

X-ray Diffraction. The purity and crystallinity of as-prepared sulfide nanowire samples were initially characterized using powder X-ray diffraction (XRD) measurements. All of the diffraction peaks observed from each of the samples can be readily indexed and have been positively ascribed to pure phases of their bulk counterparts, with lattice constants comparable to the corresponding reported database values, associated with each of the target materials. Very little if any impurity peaks were present in any of the patterns though, it should be mentioned that two very weak peaks surrounding the (111) peak of cubic phase CdS (JCPDS No. 10-0454) could be ascribed to the (100) and (101) peaks of hexagonal würtzite CdS (JCPDS No. 41-1049). Thus, overall, these results show that reasonably pure, crystalline hexagonal-phase CuS, cubic-phase PbS, and cubic-phase CdS can be prepared under ambient, room-temperature conditions without the necessity of an additional annealing step at high temperature.

The CdS results are worthy of further discussion. CdS possesses three types of crystal structures, namely hexagonal würtzite, cubic zinc blende, and high-pressure rocksalt phases. The hexagonal phase can be observed in both bulk and nanocrystalline structures, whereas the cubic and rocksalt phases are less commonly formed. Amongst the three phases, hexagonal würtzite has been intensively investigated because it is the most thermodynamically stable form of CdS and has been extensively synthesized easily by a number of groups. By contrast, only a relatively few number of papers has ever claimed the synthesis of either spherical quantum dots or cylindrical nanowires of CdS possessing either the cubic zinc blende phase or even a mixture of both hexagonal and cubic phases (Bao et al., *J. Phys. Chem. C* 2007, 111, 17527-17534; Thiruvengadathan et al., *Chem. Mater.* 2005, 17, 3281-3287; Simmons et al., *Nano Lett.* 2002, 2, 263-268; Sathish et al., *Catalysis Today* 2007, 129, 421-427). Hence, for the first time, ambient, room-temperature preparation of CdS nanowires associated with a metastable cubic phase with minimal hexagonal phase impurities has been demonstrated.

In contrast with ambiently prepared cubic phase CdS nanowires, all of the diffraction peaks corresponding to the cactus-like nanostructures, formed at higher temperatures, can be indexed to the pure hexagonal phase of CdS (JCPDS No. 41-1049). The energy difference between the cubic and hexagonal CdS energy gap differs by less than 0.1 eV (Zelaya-Angel et al., *Appl. Phys. Lett.* 1994, 64, (3), 291-293). The relative peak broadening observed can be attributed to the existence of crystalline faults, microstrains, crystalline domain sizes, and/or domain size distribution (Shen et al., *J. Phys. Chem. C* 2007, 111, 7280-7287).

Electron Microscopy.

(i). CuS.

The size and morphology of as-prepared metal sulfide 1D nanostructures have been studied using FE-SEM and TEM. The presence of dispersed individual nanorods as well as of bundled, aggregated species clearly shows that straight, smooth, and crystalline wire-like CuS 1D nanostructures, with a relatively uniform diameter throughout their entire length, can be produced. Diameters of as-prepared CuS nanowires were 100±13 nm, while measured lengths attained values of as much as several microns, comparable to the thickness (6 µm) of the PC membranes from whence these structures were derived. In addition, EDS elemental analysis data taken from SEM clearly indicate that the sample is only composed of Cu and S, with the presence of the Si peak attributable to the underlying silicon wafer.

To provide additional insight into the structure of the as-prepared sample, randomly chosen single nanowires, were analyzed by HRTEM and SAED. The HRTEM image of a portion of an individual CuS nanowire shows a single-crystalline with a lattice fringe spacing of 0.191 nm, corresponding to the (110) plane of the hexagonal phase of a CuS crystal. The SAED pattern consists of sharp spots that can be indexed to the (110) and (100) diffraction planes, respectively, of primitive hexagonal CuS. Moreover, the HRTEM image and SAED patterns taken from different positions along the nanowire were found to be essentially identical within experimental accuracy, indicating the entire nanowire can be assumed to be single-crystalline, while a thin amorphous layer likely coats at least part of the outer surface.

Due to a high rate of occupancy of the interior of the membrane pores with the precursors associated with the CuS sample, the resulting nanowires tend to form arrays, after removal of the PC template by methylene chloride with modest sonication. Arrays of CuS nanowires appear to be structurally robust and well preserved. The SEM image higher magnification clearly shows that the nanowires are individually separated from each other as opposed to forming mass aggregates, and are roughly parallel to each other so as to generate a packed, vertically aligned array architecture upon template removal.

It is evident that these nanowires form a dense, continuous network, stretching over micron-sized areas. In particular, CuS nanowire arrays, grown within the pores of PC templates, contain nanowires with diameters of ~200±18 nm and lengths measuring in the microns, corresponding to the dimensions of the originating pore channels. The possibility that a remnant residue of the polycarbonate template, interdispersed within the nanowire framework, cannot be discounted as contributing to the mechanical support for these sulfide arrays. Such a scenario is not unusual considering that due to the random nature of the pore-production process in the track-etched membrane, a number of pores may have actually intersected within the membrane itself (Hulteen et al., *J. Mater. Chem.* 1997, 7, (7), 1075-1087). Moreover, while disulfide bond formation between dangling sulfur species is a plausible causal factor, (Young et al., *Langmuir* 2007, 23, 12923-12931) it is more likely that CuS growth 'spilling' outside the pores themselves was a more important determinant, accounting for the additional reinforcing 'glue' for these arrays.

(ii). PbS.

Similarly, representative SEM and TEM images reveal that clusters of as-prepared PbS, isolated from PC membranes with 200 nm pore size diameters, primarily consist of one-dimensional structures possessing a straight, wire-like morphology with a relatively uniform diameter in the range of 200±20 nm throughout their entire length of approximately 3.7-5.6 µm. The EDS spectrum shows signals associated with Pb and S, which overlap with each other in the energy scale at around 2.3-2.7 keV. The observed Si and C peaks likely originate from the silicon wafer and conductive carbon tape, respectively. The corresponding HRTEM image of a single PbS nanowire suggests a lattice spacing of 0.298 nm, which can be indexed to the (200) plane of a face-centered cubic phase of a bulk PbS crystal (JCPDS File No. 78-1901), indicating that the nanowire likely grows in a [100] orientation. The somewhat distorted SAED pattern suggests that the nanowires are not perfectly single-crystalline in nature. Indeed, the discrete but elongated bright spots can be indexed to the (200) planes of cubic PbS, unlike the usual broad, amorphous diffraction rings, characteristic of polycrystallinity. Moreover, the data indicate that the nanowire may consist of multiple single-crystalline domains composed of highly oriented nanocrystals growing along the [100] crystallographic axis (Tong et al., *Angew. Chem. Int. Ed.* 2006, 45, 7739-7742).

(iii). CdS.

In typical SEM and TEM images of an as-prepared CdS sample, prepared under ambient conditions, it can be observed that straight and smooth nanowires with relatively uniform and homogeneous size can be routinely synthesized. Measured nanowires possess diameters spanning from 46 to 53 nm, based on the corresponding 50 nm pore sizes of the PC membranes used, and a length range of 2.1 to 4.6 µm. The resulting nanowires also tend to form reasonably robust arrays upon removal of the template. The chemical signatures obtained from the EDS spectra correspond to Cd and S elements. The Si signal arises from the underlying silicon wafer used for analysis. A representative HRTEM image illustrates the single-crystalline nature of the CdS nanowires with an interplanar spacing of ~0.338 nm, corresponding to the (111) plane of pure face-centered cubic CdS. The sharp SAED pattern confirms that the entire nanowire is likely single-crystalline in nature, with two diffraction planes, i.e. (111) and (220), that can be indexed to the cubic structure of CdS.

Figure 1B:
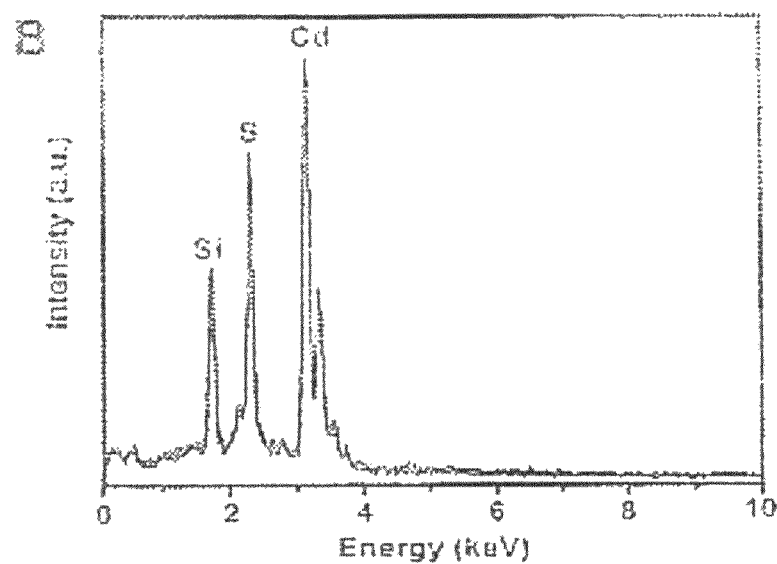
FIG. 1B. EDS spectrum of as-prepared CdS cactus-like nanostructures. The Si peak originates from the underlying silicon wafer used for data collection.
Figure 1C:
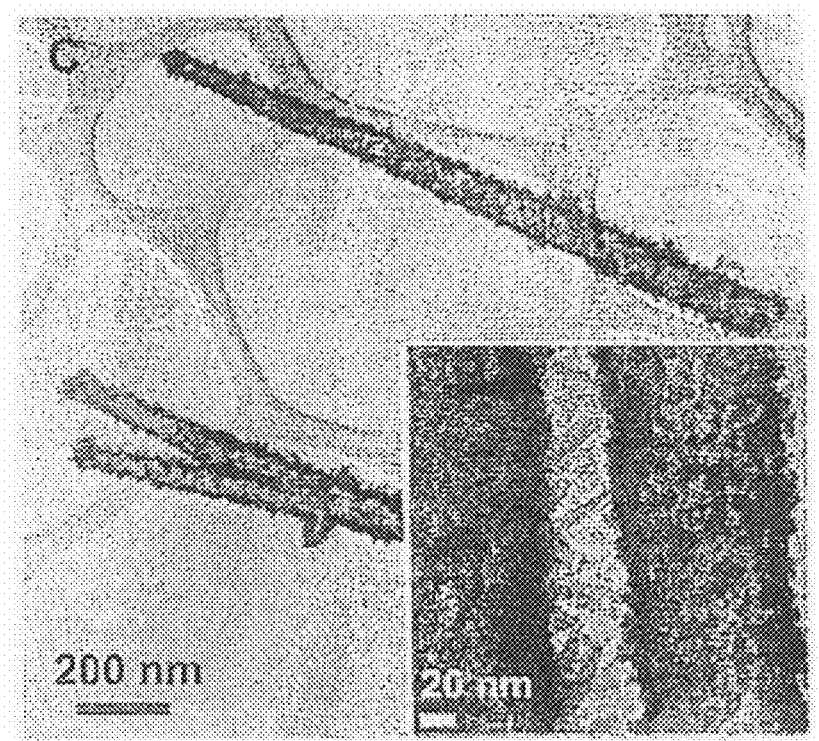
FIG. 1C. Typical TEM image of as-prepared CdS cactus-like nanostructures, prepared using polycarbonate membranes with 100-nm pore diameters at 80° C. Associated inset shows a correspondingly magnified view of as-generated products.
Figure 1D:
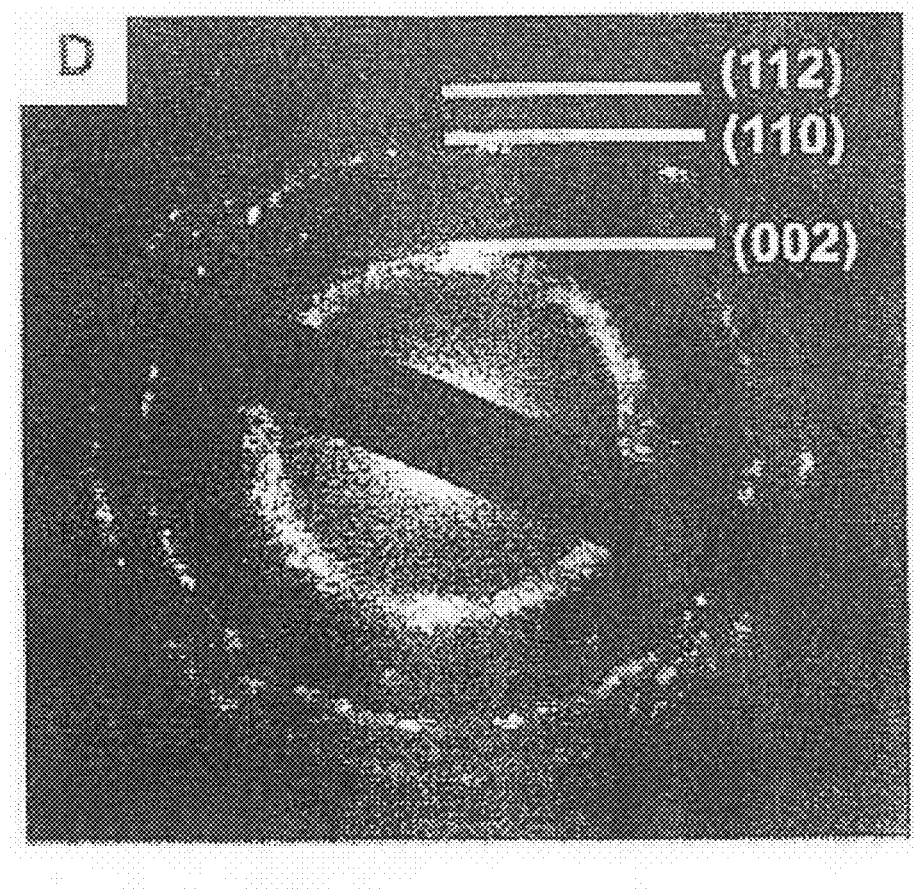
FIG. 1D. SAED pattern of a representative portion of an individual CdS cactus-like nanostructure shown in FIG. 1C.

Nanoscale CdS structures, prepared at 80° C., evinced a different morphological motif and crystallographic structure. Specifically, SEM (FIG. 1A) and TEM (FIG. 1C) images were suggestive of the formation of visibly roughened CdS nanotubes, possessing an inner diameter of ~78-90 nm, a wall thickness of ~4 nm, and average lengths of up to several microns. As indicated in the higher magnification image (inset to FIG. 1C), the roughness of these nanotubes could be attributed to the formation of needle-like, ultra-thin structures measuring ~20 nm long, projecting out, like a multitude of tiny bristles, from the surface of the outer wall. Though it is not an uncommon structural archetype, this cactus-like nanostructure has not been previously observed for CdS. As the Si signal could be ascribed to the underlying silicon wafer used for SEM imaging, EDS analysis (FIG. 1B) showed that the hollow structures were essentially composed of Cd and S, without any extraneous chemical impurity. FIG. 1D illustrates a representative SAED pattern taken from an individual cactus-like nanostructure highlighted in FIG. 1C. The three rings observed can be indexed to the (002), (110), and (112) diffraction planes, respectively, corresponding to the crystalline hexagonal phase of CdS.

Figure 2A:
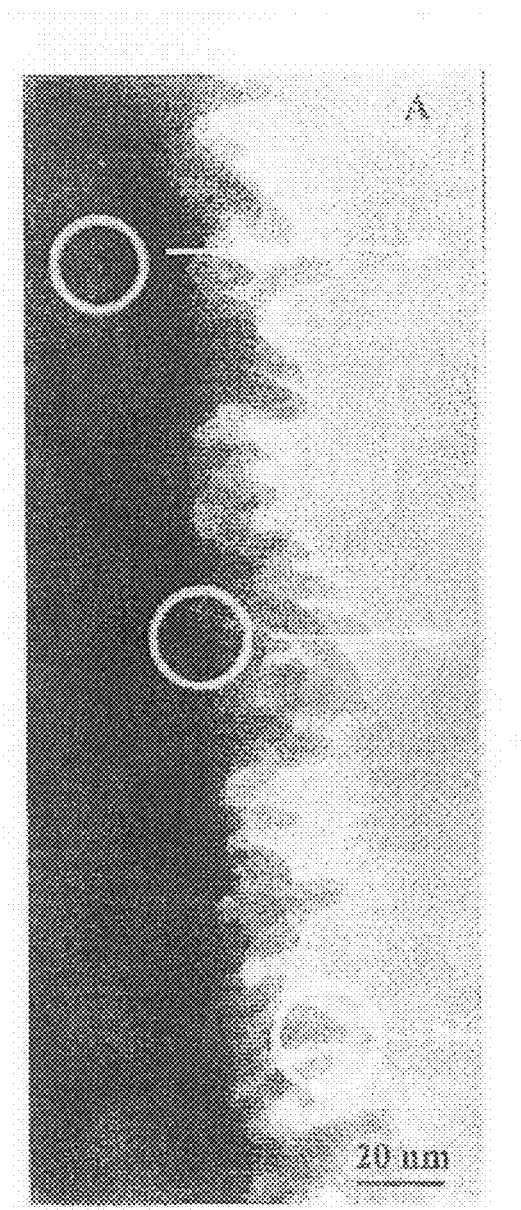
FIG. 2A. TEM image of an individual CdS cactus-like nanostructure.

FIG. 2A highlights a portion of a typical cactus-like nanostructure (e.g. inset to FIG. 1C), constructed from needle-like bristles projecting outwards and branching off from the main CdS nanotube framework. In this magnified view, it is evident that the outer wall of the tubes is almost completely covered with these thin nanoscale needles.

Figure 2B:
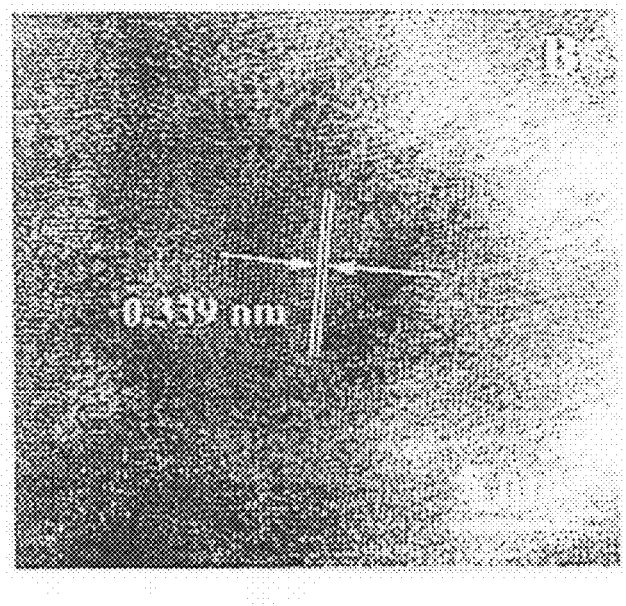
FIG. 2B. HRTEM image taken from a position, delineated by the top white circle, along a portion of the cactus-like nanostructure in FIG. 2A.
Figure 2C:
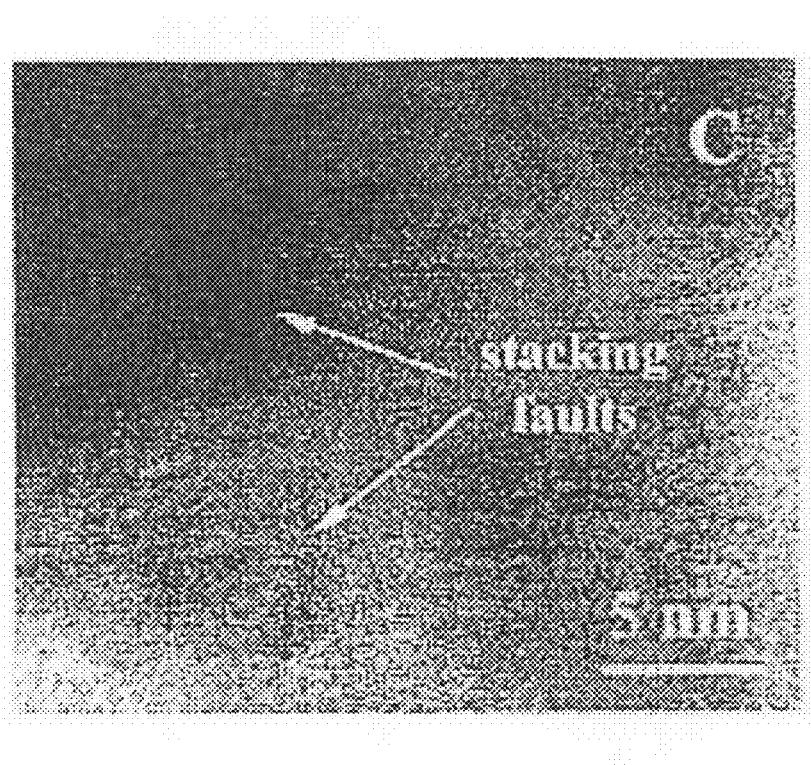
FIG. 2C. HRTEM image taken from a position, delineated by the middle white circle, along a portion of the cactus-like nanostructure in FIG. 2A.
Figure 2D:
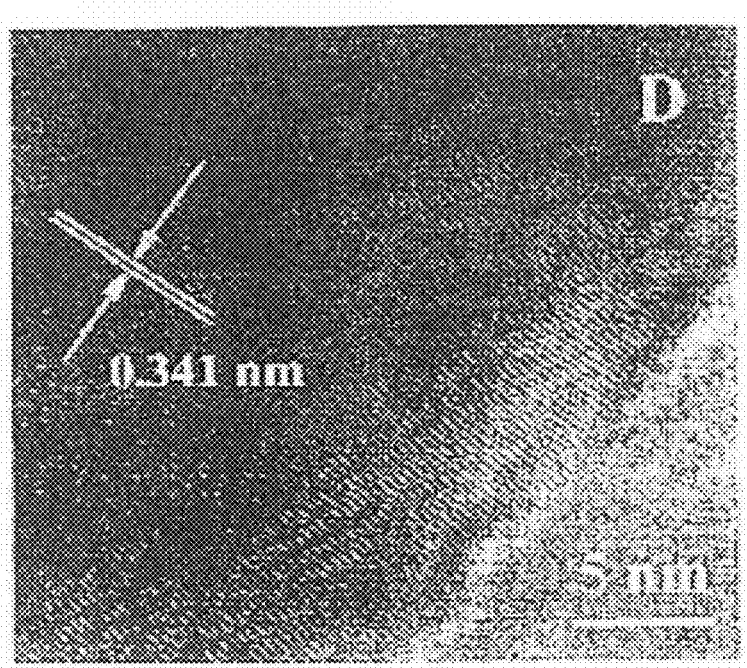
FIG. 2D. HRTEM image taken from a position, delineated by the bottom white circle, along a portion of the cactus-like nanostructure in FIG. 2A.

Representative HRTEM images were taken from three different positions along the length of the hierarchical nanostructure shown in FIG. 2A. Namely, these included the bristle-coated inner wall of the nanotube (FIG. 2B), the intersection region between the central 'trunk' and the secondary bristles (FIG. 2C), and finally, the constituent needle-like bristles themselves in a different area of the sample (FIG. 2D), respectively. The diffuse nature of the SAED pattern suggests that the entire 'trunk' may have been polycrystalline in nature and therefore, it is plausible to hypothesize that the 'trunk' may have consisted of a multitude of multi-oriented single-crystalline domains. Indeed, a lattice spacing of ~0.339 nm, obtained from one of these nanocrystals (FIG. 2B), can be ascribed to the (002) plane of a hexagonal würtzite CdS structure. Some of these nanocrystals may therefore have served as seeds for the adjoining branching structures (Dick et al., *Nature Materials* 2004, 3, 380-384). Also observed is the presence of defects such as stacking faults within the confluence areas between the central 'trunk' and its bristly 'offshoots' (FIG. 2C), similar to what has been previously described in analogous hierarchical systems (Manna et al., *J. Am. Chem. Soc.* 2000, 122, 12700-12706). Specifically, these stacking faults have been ascribed to the small energy difference between stacking sequences in the growth direction (Yao et al., *J. Phys. Chem. B* 2006, 110, 11704-11710). The bristles themselves maintain an obvious lattice spacing of ~0.341 nm, corresponding to the (002) planes of hexagonal CdS, an experimental result suggestive of the preferential [002] growth direction of these branched needle-like structures.

It is generally believed that at room temperature, single crystals of cubic CdS nanorods derived from isolated, disparate nucleation sites, which then grew by extension throughout the porous network until contact was made with the confining membrane surface itself, acting as the ultimate barrier to growth.

Without wanting to be limited by a mechanism, it is believed that the hexagonal phase cactus-like nanostructure formation at 80° C. in the absence of surfactant can be explained as follows. To account for the central nanotube "trunk," the tube-like formation is attributed to the fusion and coalescence of individual precursor particles preferentially localized along the surfaces of the template pore walls (Zhou et al., *ACS Nano* 2008, 2, (5), 944-958). The observed formation of bristles or alternatively, fractal dendritic structures, in comparable systems has been previously ascribed to the non-equilibrium growth and the inherent molecular anisotropy of the hexagonal structure of CdS (Qingqing et al., *Cryst. Growth Des.* 2006, 6, (8), 1776-1780; Ben-Jacob et al., *Phys. Rev. Lett.* 1985, 55, (12), 1315-1318). Diffusion-limited aggregation and nucleation-limited aggregation models have also been proposed to account for the formation of related complex hyperbranched structures (Yao et al., *J. Phys. Chem. B* 2006, 110, 11704-11710; Halsey et al., *Phys. Rev. Lett.* 1997, 78, 1719-1722; Ming et al., *Phys. Rev. E* 1993, 48, 621-624; Witten et al., *Phys. Rev. Lett.* 1981, 47, 1400-1403; Meakin, P., *Phys. Rev. A* 1983, 27, 1495-1507). Hence, in an alternate but plausible mechanism, with increasing temperatures, multiple nuclei, pertaining to the thermodynamically stable hexagonal phase of CdS, can form in solution in an initial nucleation stage. In the next step, these will subsequently grow to produce thin, well-crystallized CdS nanorods in the presence of additional 'monomers', which randomly move about and subsequently accumulate with other to create kinetically-roughened fractal structures (Dick et al., *Nature Materials* 2004, 3, 380-384; Peng et al., *Inorg. Chem.* 2002, 41, 5249-5254; Qin et al.; *J. Cryst. Growth* 2005, 283, 230-241; Hou et al., *Mater. Lett.* 2005, 59, 3364-3369). The lack of any definite, preferential angles with which the different branches emerged from the central trunk supports this "fractal" hypothesis herein since there were no additives present to "direct" growth (Peng et al., *Inorg. Chem.* 2002, 41, 5249-5254). Furthermore, the diffusion of smaller CdS nanostructures is known to be faster at higher temperatures, which is also conducive to their aggregation (Zhao et al., *Cryst. Growth Des.* 2008, 8, (2), 717-722).

Raman Spectroscopy. The optical properties of these sulfide 1D nanostructures were also investigated. It is well known that in a crystalline semiconductor, the observed Raman shifts are usually associated with the longitudinal optical phonons (LO), while in general, other modes, such as the transverse optical phonons (TO) and the surface phonons (SP), are not as observable because of symmetry restrictions and weaknesses in the observed intensities, respectively (Mlayah, et al., *Solid State Commun.* 1994, 90, 567-570; Nanda et al., *Appl. Surf. Sci.* 1997, 119, 50-54; Wang et al., *ACS Nano* 2008, 2, 184-190). However, these other modes can become viable due to surface roughness and crystallite size considerations as well as the large surface-to-volume ratio intrinsic to nanostructured materials. Therefore, Raman scattering measurements have become a unique tool for probing nanoscale vibrational properties, especially the exciton-phonon coupling through the Fröhlich interaction of multiexcitonic materials such as PbSe (Bierman et al., *Nano Lett.* 2007, 7, 2907-2912).

The Raman spectrum of as-prepared semiconducting nanowires corroborates the chemical identity of the as-prepared nanostructures. Specifically, a strong, sharp peak appearing at 470 cm$^{-1}$ is dominant in the spectrum of CuS nanowires, and has been previously associated with the covellite (CuS) system (Rudigier et al., *J. Appl. Phys.* 2004, 95, 5153-5158; Chen et al., *Growth Des.* 2008, 8, 2137-2143; Minceva-Sukarova et al., *J. Mol. Struct.* 1997, 410-411, 267-270), though it cannot necessarily preclude potential contributions from S—S stretching vibrational modes as well (Bastian et al., *J. Phys. Chem.* 1973, 77, (9), 1129-1133).

The Raman spectrum of PbS nanowires was analyzed. PbS is an inherently weak Raman emitter but increasing the intensity of the laser excitation might have led to sample photo-oxidation (Bierman, M. J.; Lau, Y. K. A.; Jin, S. *Nano Lett.* 2007, 7, 2907-2912). One strong peak at 143 cm$^{-1}$ is clearly observed, which can be ascribed to the SP mode (Ge et al., *Chem. Eur. J.* 2005, 11, 1889-1894; Nanda et al., *Phys. Rev. B*

1998, 58, 15405-15407). According to earlier reports (Nanda et al., *Phys. Rev. B* 1998, 58, 15405-15407; Krauss et al., *Phys. Rev. B* 1997, 55, 9860-9865), the intensity of this peak greatly increases with decreasing crystal size. However, this peak is so intense that signals at 210 and 271 cm$^{-1}$ resemble two small, secondary shoulders, corresponding to a 1 LO phonon mode and a two-phonon mode process, respectively (Wang et al., *ACS Nano* 2008, 2, 184-190; Ge et al, *Chem. Eur. J.* 2005, 11, 1889-1894). The observation also suggests that the nanowire may be composed of a substructure of small discrete nanocrystals. The weak intensity of these peaks has been previously assigned to decreasing crystallite size (Nanda et al., *Phys. Rev. B* 1998, 58, 15405-15407), which is also consistent with conclusions derived from the electron diffraction data. The Raman peak at 440 cm$^{-1}$ can be assigned to a 2 LO phonon mode, i.e. a broad overtone whose intensity is strongly dependent on the excitation wavelength (Krauss et al., *Phys. Rev. B* 1997, 55, 9860-9865). Finally, the peak at 602 cm$^{-1}$ has been previously ascribed to a second overtone signal (Wang et al., *ACS Nano* 2008, 2, 184-190).

The Raman spectrum of as-prepared CdS nanowires was analyzed. Two features of CdS are clearly evident, illustrating characteristic Raman shifts analogous to those of pure crystalline CdS (Suh et al., *Chem. Phys. Lett.* 1997, 281, 384-388). Specifically, the two peaks located at 301 and 602 cm$^{-1}$ can be assigned to the first- and second-order TO phonon modes, respectively (Zhang et al., *J. Phys. Chem. B* 2004, 108, 7002-7005), though a number of groups have claimed that these peaks actually correspond to the fundamental LO band and its associated overtone (Routkevitch et al., *Chem. Phys.* 1996, 210, 343-352; Nanda et al., *Appl. Surf Sci.* 1997, 119, 50-54; Li et al., *Inorg. Chem.* 1999, 38, 1382-1387; Kar et al., *J. Nanosci. Nanotech.* 2006, 6, 771-776). Nonetheless, the observed phonon peaks are shifted towards lower frequency than would be expected from bulk, likely due to effects of small size and high surface area. Moreover, the relatively sharp and symmetric profile (Xiong et al., *Chem. Eur. J.* 2007, 13, 3076-3081) of the peaks of the sample suggests that the nanorods are highly crystalline and relatively free of impurities, which concur with the electron microscopy data.

UV-visible Spectroscopy. The UV-visible absorption spectra of as-prepared transition metal sulfide nanowires, collected at room temperature, were analyzed. The absorption spectrum of CuS nanowires, which has been attributed by one group to partial oxidation of the nanowire surface (Wang et al., *J. Cryst. Growth* 2007, 299, 386-392), showed a broad band in the spectral region between 300 and 650 nm. This result is in general agreement with prior reports (Chen et al., *Cryst. Growth Des.* 2008, 8, 2137-2143; Wang et al., *Mater. Chem. Phys.* 2008, 109, 77-81; Jiang et al., *J. Mater. Chem.* 2000, 10, 2193-2196), with small peaks observed around 400 nm (i.e. 3.10 eV), potentially attributable to the nanorod morphology of the samples (Singh et al., *Chem. Mater.* 2007, 19, 2446-2454). Previous studies (Haram et al., *J. Phys. Chem.* 1996, 100, 5868-5873) have shown that covellite CuS also possesses a characteristically broad absorption band beyond 800 nm, that extends as a long absorption tail into the near-IR region and that can be ascribed to an electron-acceptor state lying within the bandgap (Kalyanikutty et al., *Chemical Physics Letters* 2006, 432, (1-3), 190-194; Xu et al., *Mater. Lett.* 2006, 60, 2203-2206; Gao et al., *Chem. Mater.* 2008, 20, 6263-6269). The observed data are consistent with this interpretation.

The absorption spectrum of as-prepared PbS nanowires was analyzed. It has been reported that isotropic spheres of PbS with a size less than 18 nm showed regular red-shifted excitonic absorption peaks from the visible to the infrared region with increasing particle size (Peterson et al., *Nano Lett.* 2006, 6, 510-514; Watt et al., *Mater. Lett.* 2005, 59, 3033-3036). A red shift in absorption corresponding to 60 nm as compared with 30 nm PbS nanowires has also been observed (Wu et al., *Mater. Lett.* 2007, 61, 4659-4661). A similar behavioral trend has been detected here with the relatively large-diameter nanorods. Nonetheless, the position of the absorption peak itself at 783 nm (i.e. 1.58 eV) is in agreement with a previous report (Ye et al., *J. Cryst. Growth* 2005, 284, 172-175). By comparison, the expected PbS bulk absorption edge occurs at 3024 nm (Sun et al., *Chem. Int. Ed.* 2008, 47, 3215-3218; Wang et al., *Cryst. Growth Des.* 2008, 8, 2660-2664). One plausible hypothesis for this observation, which was supported by the HRTEM/SAED data, is that the nanowires may consist of multiple single, crystalline domains composed of highly oriented nanocrystals smaller than the representative Bohr exciton radius of PbS (Wise, F. W. *Acc. Chem. Res.* 2000, 33, 773-780). Another reasonable explanation put forward for the presence of the excitonic absorption peak is that there are little if any surface defect sites on the nanorods that can trap electron-hole pairs generated by light. By contrast, it was noted that PbS nanowires measuring 16 and 35 nm in diameter did not show any distinctive maximum in the infrared region of their absorption spectrum. The absence of such a sharp, band-edge absorption feature has also been attributed to convolution of absorption peaks from nanowires of different diameters as well as to the lack of confinement in the axial dimension of the wire (Yong et al., *Chem. Mater.* 2006, 18, 5965-5972).

The UV-visible absorption spectrum of CdS nanowires was analyzed. The nanowires show a well-defined absorption feature at 498 nm (i.e. 2.49 eV), which can be ascribed to the first exciton peak of CdS (Xiong et al., *J. Mater. Chem.* 2002, 12, 3712-3716). This signal is considerably blue-shifted relative to the characteristic bulk band gap for hexagonal-phase CdS crystals (512 nm). In fact, the existence of a hexagonal CdS nanoscale impurity, the so-called minority phase, within the majority cubic phase was suggested by the XRD pattern and thus, may have contributed to the observed UV absorption signal. These data are fully consistent with previous results (Yao et al., *J. Phys. Chem. B* 2006, 110, 11704-11710; Zhao et al., *Cryst. Growth Des.* 2008, 8, (2), 717-722; Wang et al., *J. Alloys Compd.* 2008, 461, 418-422; Yong et al., *J. Phys. Chem. C* 2007, 111, 2447-2458; Nair et al., *J. Mater. Chem.* 2006, 16, 467-473; Liu et al., *J. Cryst. Growth* 2006, 290, 592-596; Maleki et al., *Mater. Lett.* 2008, 62, 1993-1995; Spahnel et al., *J. Am. Chem. Soc.* 1990, 112, 2278-2284; Ma et al., *Materials Research Bulletin* 2005, 40, (12), 2180-2188.). It is worth noting that as the cubic phase of CdS is not known in bulk form (Banerjee et al., *J. Phys.—Condens. Mater.* 2000, 12, 10647-10654), a direct band gap comparison could not be made.

While the origin of the observed blue shift, if real as it is convoluted with the broadness of the measured spectra, in all of these sulfide systems is debatable, one general explanation that has been put forward is that in semiconductors, even if the average radius of the nanostructures were to be larger than that of the exciton Bohr radius, the Coulombic energy component is dominant (Singh et al., *Chem. Mater.* 2007, 19, 2446-2454). Hence, motion (e.g. translational degrees of freedom) of the exciton, which behaves as a quasiparticle, experiences size quantization, thereby accounting for the shift to the blue (Yoffe, A. D. *Adv. Phys.* 2002, 51, (2), 799-890).

Photoluminescence Spectroscopy. The photoluminescent activity of all of the as-prepared transition metal sulfide nanowires was also probed. The room-temperature PL spectrum of the CuS nanowire sample dispersed in water shows that under an excitation wavelength of 370 nm, the sample evinced an emission peak at 423 nm. Although the exact mechanism for explaining the nature of PL emission remains controversial, prior literature suggests that the nature of the emission spectrum depends on the morphology and inherent microstructure of the sample itself. For instance, CuS needle-like fibers did not appear to evince any PL signal (Jiang et al., *J. Mater. Chem.* 2000, 10, 2193-2196) in the range of 400-800 nm. However, polycrystalline CuS nanorods have been found to possess two emission peaks at 414 and 437.5 nm, upon excitation at 371.5 nm (Ou et al., *Mater. Chem. Phys.* 2005, 94, 460-466), while as-prepared CuS/C cables yielded a broad but weak emission peak at 465 nm upon excitation at 370 nm (Chen et al., *Cryst. Growth Des.* 2008, 8, 2137-2143). Moreover, hollow spheres composed of polycrystalline nm-sized CuS crystals were associated with a broad emission with a maximum at 526 nm upon excitation at 406 nm (Yu et al., *Adv. Funct. Mater.* 2007, 17, 1397-1401). That result was explained by the presence of surface defects and an interface coupling effect between grain boundaries, thereby leading to an increase in wave-function overlap and contributing to a narrower observable bandgap. Nonetheless, the sharp excitonic emission herein indicates that the as-prepared CuS nanowires are likely of high optical quality, since nanorods with stacking fault defects have been found to exhibit poor photoluminescence (Roy et al., *Cryst. Growth Des.* 2008, 8, 1530-1534).

The room-temperature photoluminescence spectrum of the obtained PbS nanowires with an excitation wavelength of 495 nm was analyzed. The fluorescence of PbS nanostructures is generally rather weak in intensity, but detectable in the visible region (Machol et al., *Phys. A* 1994, 207, 427-434). A rather sharp PL band has been clearly observed at 794 nm (i.e., red fluorescence) and is blue shifted as compared with bulk (Ye et al., *J. Cryst. Growth* 2005, 284, 172-175; Acharya et al., *J. Am. Chem. Soc.* 2008, 130, 4594-4595). Others have reported a PL peak for nanoscale PbS in the 655-665 nm range, which has been ascribed to a transition associated with the lowest energy exciton (Chen et al., *Surf. Sci.* 2007, 601, 5142-51471 Gao et al., *Nano Lett.* 2001, 1, 743-748; Patla et al., *Nano Lett.* 2007, 7, 1459-1462). The results are in agreement with and understandably red-shifted with respect to data obtained on <10 nm PbS nanoparticles, wherein the strong emission response was assigned to band edge luminescence (BEL) (Peterson et al., *Nano Lett.* 2006, 6, 510-514; Chen et al., *Chem. Mater.* 2000, 12, 3864-3870; Kim et al., *J. Lumin.* 2006, 119-120, 214-218). Again, the observations are consistent with the idea that the as-prepared nanowires may be plausibly composed of multiple single domains of PbS quantum dots.

The PL spectrum of as-prepared CdS nanowires, obtained with an excitation wavelength of 400 nm at room temperature, was analyzed. Though the intensity of the peak has been previously attributed to the presence of surface defects (Thiruvengadathan et al., *Chem. Mater.* 2005, 17, 3281-3287), a relatively sharp emission peak at 547 nm was detected, analogous to previously reported results (Simmons et al., *Nano Lett.* 2002, 2, 263-268; Wang et al., *Chem. Mater.* 2002, 14, 3028-3033). This band has been ascribed to near-band-edge (NBE) emission, originating from the recombination of excitons and/or shallowly trapped electron hole pairs within surface states (Xiong et al., *Chem. Eur. J.* 2007, 13, 3076-3081; Zhan et al., *Adv. Mater.* 2000, 12, 1348-1351; Kar et al., *J. Nanosci. Nanotech.* 2006, 6, 771-776; Liu et al., *J. Cryst. Growth* 2006, 290, 592-596; Wang et al., *Chem. Mater.* 2002, 14, 3028-3033; Kar et al., *J. Phys. Chem. B* 2006, 110, 4542-4547). Also noted is the relative narrowness of the PL peak, coupled with the lack of a strong emission near 600 nm from deep levels associated with defects (such as vacancies and interstitials) (Zhao et al., *Cryst. Growth Des.* 2008, 8, (2), 717-722; Mondal et al., *Mater. Sci. Semicond. Proc.* 2007, 10, 185-193) and impurities (Barrelet et al., *J. Am. Chem. Soc* 2003, 125, 11498-11499; Pike et al., *Thin Solid Films* 1993, 224, 221-226). In fact, the lack of a broad, longer-wavelength, trap emission state, which would have resulted from an excess of either sulfur or cadmium at the interface and which is known to quench radiative recombination of electron hole-pairs (Hsu et al., *Langmuir* 2004, 20, 23-26), strongly suggests the high degree of purity of the samples. Overall, the results intimate that the single-crystalline nanowires have high-quality optical properties, critical for photonic device applications, and also possess a reasonable size monodispersity in terms of diameter and length (Xi et al., *Chem. Mater.* 2008, 20, 5444-5452).

Photocatalytic Activity.

In terms of photoinduced degradation reactions, it is known that under UV light irradiation, in the presence of CdS nanocrystals, halogenated benzenes are often dehalogenated, yielding trichlorobenzene from hexachlorobenzene and tetrafluorobenzene isomers from hexafluorobenzene as the final products (Yin et al., *Environ. Sci. Technol.* 2001, 35, 227-231). It is obvious though that the analogous roles of crystal phase, grain size, phase composition, and dimensionality have not been determined for photodegradation reactions of non-biodegradable organic dyes, which are model organic substrates, representative of organic pollutant systems.

Thus, reasonably simple reactions were probed involving the degradation of Rhodamine B and methyl orange under UV irradiation conditions in the presence of CdS (Li et al., *J. Phys. Chem. C* 2008, 112, 14943-14947; Guo et al., *J. Phys. Chem. B* 2005, 109, 21602-21607). The photocatalytic potential of as-prepared CdS nanowires was evaluated by monitoring the optical behavior of Rhodamine B (RhB) and methyl orange (MO) at their peak absorbances upon photoexcitation with UV light at 366 nm. Noted was a continual fading of the coloration of both RhB and MO solutions as function of reaction time, in the presence of either CdS nanowires, cactus-like nanostructures, or commercial bulk samples, implying a steady, continuous degradation of the organic dyes.

The photocatalytic performance of CdS was estimated by monitoring the intensity of RhB's characteristic absorption at 555 nm as a function of reaction time. The data clearly showed that nanowires, cactus-like nanostructures, and the bulk sample are active photocatalysts. In addition, both CdS nanowires and cactus-like nanostructures exhibited a higher photocatalytic degradation activity as compared with the bulk sample. The photocatalytic activity of CdS was also evaluated by probing the analogous degradation of MO molecules in water, by measuring changes in absorption at 464 nm as a function of reaction time. Similar trends were observed in that the CdS nanowires and cactus-like nanostructures yielded an appreciably higher activity as compared with bulk behavior. As control experiments, almost no dye degradation in solution was observed, in the absence of CdS catalyst, similarly subjected to UV light irradiation.

The photocatalytic decolorization reaction of RhB can be modeled as a pseudo-first-order reaction with the kinetics expressed by the equation, $\ln(C_0/C_t)=kt$, where $C_0$ represents the initial concentration of aqueous RhB, $C_t$ denotes the concentration of RhB at a given reaction time 't', and k is the reaction rate constant. From the linear extrapolations, the computed reaction rate constants of the CdS cactus-like nanostructures, nanowires, and bulk sample are $1.2 \cdot 10^{-2}$ min$^{-1}$, $9.5 \cdot 10^{-3}$ min$^{-1}$, and $4.9 \cdot 10^{-3}$ min$^{-1}$, respectively. For the corresponding degradation rates of MO in the presence of these various CdS morphologies, calculated first-order reaction rate constants of $7.6 \cdot 10^{-3}$ min$^{-1}$, $5.5 \cdot 10^{-3}$ min$^{-1}$, and $2.6 \cdot 10^{-3}$ min$^{-1}$ for CdS cactus-like nanostructures, nanowires, and bulk samples, respectively, were demonstrated.

The potential photocatalytic mechanism in the degradation of RhB and MO has been previously described and may involve several steps: (1) photoabsorption of the CdS catalysts, (2) generation of photoinduced electrons and holes, (3) transfer of charge carriers to the surface, and (4) recombination of the available charge carriers with reactive, reagent dye molecules (Li et al., *J. Phys. Chem. C* 2008, 112, 14943-14947). The observed enhancement of photocatalytic activity of the as-prepared nanowires and cactus-like nanostructures herein is most likely correlated with an increase in the purity, crystallinity, and availability of surface reactive sites of the samples as compared with the bulk. This structural morphology-dependent trend is also consistent with previous results on analogous semiconducting nanoparticle systems (Mao et al., *J. Am. Chem. Soc.* 2006, 128, 8217-8226; Zhou et al., *ACS Nano* 2008, 2, (5), 944-958). Moreover, in the case of cactus-like nanostructures, the hexagonal phase CdS is generally considered to be the more efficient phase for photocatalysis-related applications (Matsumura et al., *J. Phys. Chem.* 1985, 89, 1327-1329; Silva et al., *J. Phys. Chem. C* 2008, 112, 12069-12073).

A previous report on the photocatalytic degradation of RhB, under identical UV light irradiation conditions in the presence of cubic CdS nanocrystals measuring ~3 nm implanted in a metal hydroxide layer matrix, showed that the amount of observed dye decomposition was up to 95% after 100 min of UV light irradiation (Guo et al., *J. Phys. Chem. B* 2005, 109, 21602-21607). By contrast, the unbound samples necessitated about 135 min to achieve an identical degree of dye degradation. The superior photocatalytic performance of these nanocrystals was attributed to the more effective migration of photoinduced holes and electrons to the nanoparticle surface and their associated trapping at the interface between the nanoparticle and its solid layer matrix.

Further Observations

The present invention includes the demonstration of a reliable, reproducible, room-temperature synthesis, using a modified template-directed methodology, of crystalline semiconducting metal sulfide (CuS, PbS, and CdS) nanowires, with various controllable sizes and shapes including vertically-aligned arrays and temperature-dependent cactus-like assemblies. The porous channels of the polycarbonate membranes not only enable the continuous flow of precursor solution but also provide for a spatially constrained environment to direct the growth of sulfide nanowires. Structural imperfections in the samples, such as protrusions and depressions, directly reflect the interior nanoscopic profiles of the templates pore channels from whence these nanomaterials were derived. Resulting 1D nanostructures have been extensively characterized using a variety of diffraction, electron microscopy and optical spectroscopy techniques. Moreover, it has been demonstrated that as-prepared CdS nanowires, possessing a pure cubic phase can be used in the photocatalytic degradation of organic dyes.

Phosphate Nanostructures

A simple and effective template-mediated protocol has been developed for the large-scale, room-temperature preparation of high-aspect-ratio, single-crystalline Rare-Earth phosphate nanowires. For example, some Tb-doped CePO$_4$ nanowires measure ~12 nm in diameter and over 10 microns in length. Moreover, sheaf-like bundles of nanostructures were also isolated. The synthesis mechanism likely involved a crystal splitting step. The resulting nanowires demonstrated an intense redox-sensitive green photoluminescence, which was exploited, in addition to their inherently high biocompatibility and low toxicity, for applications in biomedical detection and labeling of cells.

Experimental Section

Synthesis. Polycarbonate track-etched membranes, measuring ca. 6 μm in thickness, can contain pore sizes of either 15, 50, 100, or 200 nm diameter, and were purchased from Whatman Co., UK. The membranes were initially hydrated by immersion and sonication in a small volume of distilled, deionized water for a few minutes, so as to limit the formation of air bubbles either within their interior pore structures or on their exterior surfaces. Subsequently, the membrane was mounted between two half arms of a U-shaped tube. In a typical ambient synthesis, one of the two half cells was filled with a 0.01 M NaH$_2$PO$_4$ (Fisher Scientific; 99.1%) solution, which was adjusted to acidic reaction conditions (e.g. pH values from 2 to 6) using HCl, and the other half cell contained a solution by mixing 0.05 M CeCl$_3$ (Aldrich, 99.9%) solution together with Tb(NO$_3$)$_3$ (Alfa Aesar, 99.9%) up to a final molar concentration of 10.0%, so as to generate desired Tb-doped CePO$_4$ nanostructures. The system was then left unperturbed for an incubation period of only 2 h at room temperature. It is noteworthy that varying the concentrations of NaH$_2$PO$_4$ from 0.001 M to 0.05 M and of CeCl$_3$ from 0.005 M to 0.25 M (with the Tb content adjusted to provide for a final molar concentration of 10.0%) yielded essentially identical results in terms of ultimate product morphology.

Subsequent to immersion, the half cell containing both CeCl$_3$ and Tb(NO$_3$)$_3$ solutions became occluded in nature, and a white precipitate was obtained after centrifugation. To isolate products within the template itself, the polycarbonate membrane was detached, sonicated for about 2 min to remove the unwanted particles on the surface, and thoroughly washed with distilled water, before being dissolved again with methylene chloride. As-prepared phosphate nanostructures were isolated from solution by centrifugation upon washing.

Characterization. As-prepared samples were thoroughly characterized using a number of different methodologies, including powder X-ray diffraction (XRD), field-emission scanning electron microscopy (FE-SEM), transmission electron microscopy (TEM), high resolution TEM (HRTEM), selected area electron diffraction (SAED), and energy-dispersive X-ray spectroscopy (EDS), as well as with UV-Visible and photoluminescence (PL) spectroscopies.

X-ray Diffraction. Crystallographic and purity information on the as-prepared phosphate nanostructures were initially obtained using powder X-ray diffraction (XRD). To prepare samples, the resulting nanowire samples were rendered into slurries in ethanol, sonicated for about 1 min, and then air-dried upon deposition onto glass slides. Diffraction patterns were subsequently collected using a Scintag diffractometer, operating in the Bragg configuration using Cu Kα radiation ($\lambda$=1.54 Å) ranging from 10 to 80° at a scanning rate of 2° per minute.

Electron Microscopy. The morphology and size distribution of the resulting phosphate nanowires were initially characterized using a field emission SEM (FE-SEM Leo 1550) at accelerating voltages of 15 kV and equipped with EDS capabilities. Specifically, samples for SEM were prepared by dispersing as-prepared phosphate nanowires in ethanol, sonicating for about 2 min, and then depositing them onto a silicon wafer, attached to a SEM brass stub using conductive carbon tape. All of these samples were subsequently conductively coated with gold by sputtering for 15 s so as to minimize charging effects under SEM imaging conditions.

Low magnification transmission electron microscopy (TEM) images were taken at an accelerating voltage of 80 kV on a FEI Tecnai12 BioTwinG$^2$ instrument, equipped with an AMT XR-60 CCD Digital Camera System. High-resolution transmission electron microscopy (HRTEM) images and SAED patterns were obtained on a JEOL 2010F instrument at accelerating voltages of 200 kV. Specimens for all of these TEM experiments were prepared by dispersing the as-prepared product in ethanol, sonicating for 2 min to ensure adequate dispersion of the nanowires, and dipping one drop of the solution onto a 300 mesh Cu grid, coated with a lacey carbon film.

Optical Spectroscopy. UV-visible spectra were collected at high resolution on a Thermospectronics UV1 spectrometer using quartz cells with a 10-mm path length. Spectra were obtained for as-prepared phosphate nanorods, which were then sonicated in distilled water so as to yield homogeneous dispersions. UV-visible absorption spectra were recorded using distilled water as a blank.

Samples for PL spectra were dispersed in deionized water and sonicated for 1 min. Fluorescence data were subsequently obtained at room temperature on a Jobin Yvon Spex Fluoro-Max-4 with a 10 s integration time, using an excitation wavelength of 256 nm.

In order to test luminescence switching behavior, $KMnO_4$ and ascorbic acid were used to oxidize and reduce $Ce^{3+}$, respectively, in each cycle. As-treated samples were washed by water several times in order to eliminate impurities prior to measurement.

Biological Experiments. The viability of as-prepared $Tb^{3+}$-doped cerium phosphate nanowires was tested as fluorescent biological labels for in vivo bioimaging. Prior to processing, the Tb-doped $CePO_4$ nanowires were sonicated for about 1 hour in order to shorten their lengths so as to assist their biological incorporation. Cell Culture. (Jiang, J. et al. *Adv. Mater.* 2008, 20, 4403-4407; Guo, S.-R. et al. *Adv. Funct. Mater.* 2008, 18, 872-879). Human cervical cancer (HeLa) cells were initially propagated onto 100 mm-diameter tissue culture dishes in DMEM medium (Life Technologies, GIBCO), supplemented with 10% fetal bovine serum (FBS) at 37° C. in a humidified atmosphere containing 5% $CO_2$. At confluence, the cells were washed, trypsinized, and resuspended in culture medium. HeLa cells were seeded at a concentration of $10^4$ cells/well on 12 mm-diameter glass cover slips in 24-well tissue culture plates, and allowed to grow for 24 h at 37° C. under 5% $CO_2$. Nanowires were subsequently added at different concentrations ranging from 0.1 to 0.5 mg/mL into the culture medium, and cells were grown for either an additional 2 h or 24 h at 37° C. under a 5% $CO_2$ atmosphere. Subsequently, the cell medium was removed, and cells on the coverslips were washed with phosphate buffered saline (PBS) three times so as to clear free nanowires from both the medium and the cell surface, prior to imaging. Confocal Microscopy (CFM) Imaging. Cells treated as described above were resuspended in 100 μL of PBS after each experiment, and dropped onto an uncoated bottom glass dish (MatTek Corp.). CFM experiments aimed at assessing cellular uptake, localization, and fluorescent signaling of the nanowires were subsequently performed using a Zeiss LSM 510 META NLO two-photon laser scanning confocal microscope system, operating at around a 380 nm excitation wavelength using a tunable Chameleon XR laser system and a 505 nm longpass filter. Images were captured using either a C-Apochromat 63×/1.2 Water (corr.) objective or a Plan-Apochromat 100×/1.45 oil objective. Acquired data were analyzed using the LSM 510 META software. Orthogonal sectioning images were recorded within the cells by focusing on the xy plane along the z axis, the yz plane along the x axis, and the xz plane along they axis, respectively. *Cell Cytotoxicity* Guo, (S.-R. et al. *Adv. Funct. Mater.* 2008, 18, 872-879). A tetrazolium salt, 3-(4,5-dimethylthiazol-2-yl)-2,5-diphenyltetrazolium bromide (MTT), assay of HeLa cells was performed to test the cytotoxicity of as-prepared products. In this assay, cells were seeded in a 96-well microplate at a density of 5000 cells per well. After 24 h of incubation, the nanowires were directly added to the culture medium at different concentrations ranging from 0.1 to 0.5 mg/mL, and the plate was incubated for another additional 2 h to 48 h at 37° C. At the end of the cell culture incubation, MTT was added into each well. After processing for 4 h, all media were removed and acidic ethanol was added to each well before absorbance was measured by a microplate reader. The following formula was used to calculate the degree of inhibition of cell growth: cell viability (%)=(mean of Absorbance value of treatment group/mean Absorbance value of control)*100%. (Hu, H. et al. *Chem. Mater.* 2008, 20, 7003-7009).

Results and Discussion

X-ray Diffraction. The purity and crystallinity of as-prepared Tb-doped $CePO_4$ nanowires were initially characterized using XRD. All of the diffraction peaks observed from the sample can be readily indexed to a pure hexagonal phase formulation [space group: $P6_222$] of pristine $CePO_4$, possessing lattice constants of $\alpha=7.103$ Å and $c=6.481$ Å, which are comparable with reported database values of $\alpha=7.055$ Å and $c=6.439$ Å for bulk $CePO_4$ (JCPDS File No. 34-1380). Moreover, the intensity of the (200) peak is much stronger than that of the other peaks, and is distinctly different from that of bulk hexagonal $CePO_4$. Nonetheless, the data indicate that the as-obtained nanowires should grow preferentially along the [001] direction (the c-axis), an assertion which is further demonstrated below by HRTEM and SAED analysis.

Electron Microscopy

Insights into Nanowire Formation. The size and morphology of the as-prepared Tb-doped $CePO_4$ nanowires, collected from the U-tube solution outside the actual templates themselves, were investigated using both FE-SEM and TEM. A very large number of nanowires could be isolated, no matter what pore size dimension (e.g. 50, 100, or 200 nm) of polycarbonate membranes was used in the synthesis. In fact, for a typical reaction time of 2 h, about 600 mg per experimental run were collected, corresponding to a reasonable 60 to 65% yield. The large quantities of nanowires synthesized are atypical of conventional template syntheses but were fully representative of the results associated with the modified protocol for the phosphate system of the present invention.

Based on measurements of several tens of nanowires pertaining to each of the samples, the as-prepared nanowires measured 14±5 nm in diameter with a length of up to 10±2 micrometers. Curiously, these lengths were much longer than the reported thickness of the membrane (e.g. 6 μm), and measured diameters were much thinner than the smallest pore diameters normally used (e.g. 50 nm). In additional experiments, when a number of syntheses using membranes with pore sizes measuring as small as 15 nm were performed, the resulting nanowires possessed diameters ranging from 8 to 12 nm with lengths of 7 to 11 microns. Though these ultrathin nanowires tended to aggregate and cluster fairly easily, as observed from the SEM image, sonication could readily resolve this problem, resulting in the isolation of individual nanostructures, as observed in TEM image.

The HRTEM image of a randomly chosen individual Tb-doped $CePO_4$ nanowire clearly shows resolvable planes corresponding to the (001) and (100) directions. The (001) planes are oriented parallel to the nanowires' growth axis, suggesting that the growth direction of the single-crystalline nanowire occurs preferentially along the [001] direction (the c-axis). By contrast, the SAED pattern taken from single nanowires can be indexed to the (100) and (001) planes of a hexagonal $CePO_4$ single crystal phase, respectively. These findings are consistent with previous XRD analyses. EDS analysis confirms that the chemical signatures associated with the nanowires are composed of Tb, Ce, P, and O elements, while the Cu signal originates from the TEM grid.

The interesting nuances of the template experiments herein are associated with two factors in particular. First, significantly thinner and shorter nanowires in the U-tubes (but not from the membrane pores themselves) were synthesized than otherwise might have been expected based upon the pore diameter and membrane thickness from whence these nanomaterials were derived. Second, hundreds of mg of product could easily be generated in a given experiment as opposed to merely synthesizing a few tens of mg at a given time, as was typical of much of previous work (Mao et al., *J. Am. Chem. Soc.* 2004, 126, 15245-15252; Mao et al., *Adv. Mater.* 2006, 18, 1895-1899; Zhou et al., *ACS Nano* 2008, 2, 944-958; Zhou et al., *J. Solid State Chem.* 2008, 181, 1539-1545; Zhang et al., *Adv. Funct. Mater.* 2008, 18, 103-112; Zhang et al., *Chem. Mater.* 2008, 20, 5500-5512; Zhang et al., *J. Phys. Chem. C* 2008, 112, 14816-14824). It would have been expected that the morphology of the Tb-doped $CePO_4$ nanorods would have faithfully mapped out the interior spatial profile, dimensionality, and localized contours of the internal pore channels of the polycarbonate membrane scaffolds from whence these 1D structures were produced. This simplistic mechanism did not play out.

From a structural point of view, hexagonal $CePO_4$ consists of infinite linear chains of alternating cerous and phosphate ions, extending along the c-axis. From a thermodynamic perspective, the bonding between these chains is considerably weaker than that within the chains, such that the activation energy for the c-axis direction of growth of hexagonal $CePO_4$ is lower than that for a growth direction perpendicular to the c-axis itself (Murphy et al., *J. Appl. Phys.* 1977, 48, 4122-4131). Hence, these data imply a higher growth rate along the c-axis, suggesting that the nanorods end up growing preferentially and anisotropically along the [001] direction (Chen et al., *J. Phys. Chem. C* 2008, 112, 20217-20221; Yan et al., *Chem.—Eur. J.* 2005, 11, 2183-2195; Fang et al., *J. Am. Chem. Soc.* 2003, 125, 16025-16034; Stavila et al., *Chem. Mater.* 2009, 21, 5456-5465). Thus, the intrinsic crystal structure of $CePO_4$ itself is inherently responsible for the observed 1D growth (Peng et al., *J. Am. Chem. Soc.* 2001, 123, 1389-1395; Peng et al., *J. Am. Chem. Soc.* 2002, 124, 3343-3353). One other key point to note is that the synthesis is pH-dependent, which can help to define the local chemical potential (Fang et al., *Cryst. Growth Des.* 2005, 5, 1221-1225). The pH parameter (Fang et al., *J. Am. Chem. Soc.* 2003, 125, 16025-16034) can sensitively influence the solute concentrations of both cerous and phosphate ions. A hexagonal-phase $CePO_4$ nanorod morphology was obtained when the pH value was acidic, presumably aided by enhanced dissolution of cerous and phosphate ions under these conditions, thereby allowing the ions sufficient time and opportunity to adopt correct positions within the developing crystal lattices (Yan et al., *Solid State Commun.* 2004, 130, 125-129; Zhang et al., *J. Cryst. Growth* 2003, 256, 156-161).

Figure 3A:
FIG. 3A. Typical SEM image of sheaf-like bundles of as-prepared Tb-doped $CePO_4$ nanostructures grown the 100 nm pore channels of polycarbonate membranes.
Figure 3B:
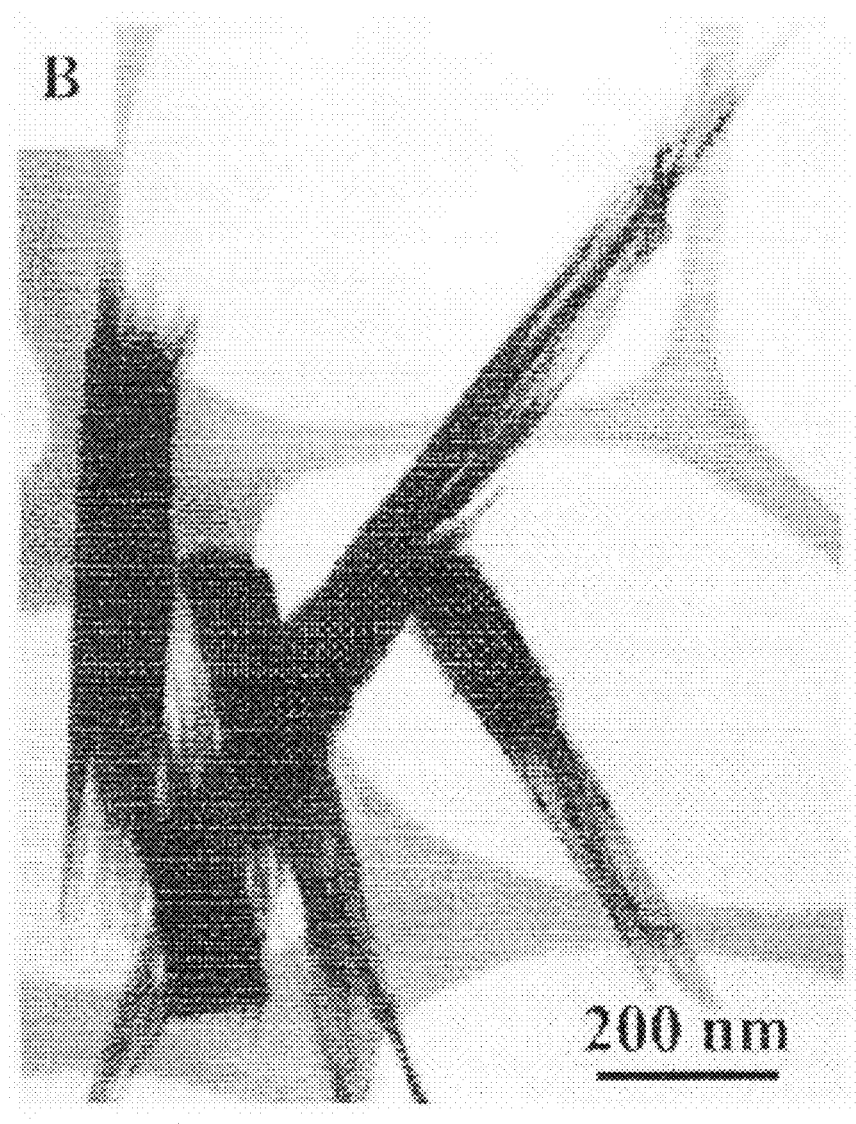
FIG. 3B. Typical TEM image of sheaf-like bundles of as-prepared Tb-doped $CePO_4$ nanostructures grown the 100 nm pore channels of polycarbonate membranes.

Insights into Sheaf-like Bundle Formation. Sheaf-like bundles of Tb-doped $CePO_4$ nanostructures were synthesized to the tune of ~50 mg per run, corresponding to a ~5% yield, upon removal of the template membrane itself. FIG. 3A and B are representative SEM and TEM images of these atypical morphologies. Specifically, each sheaf-like bundle measures ~100 nm in width, comparable to the pore width of the polycarbonate membrane. Individual constituent bristles of each bundle possess an average diameter of ~12 nm, comparable in dimension with that of the thin nanowires collected in the solution.

Figure 3C:
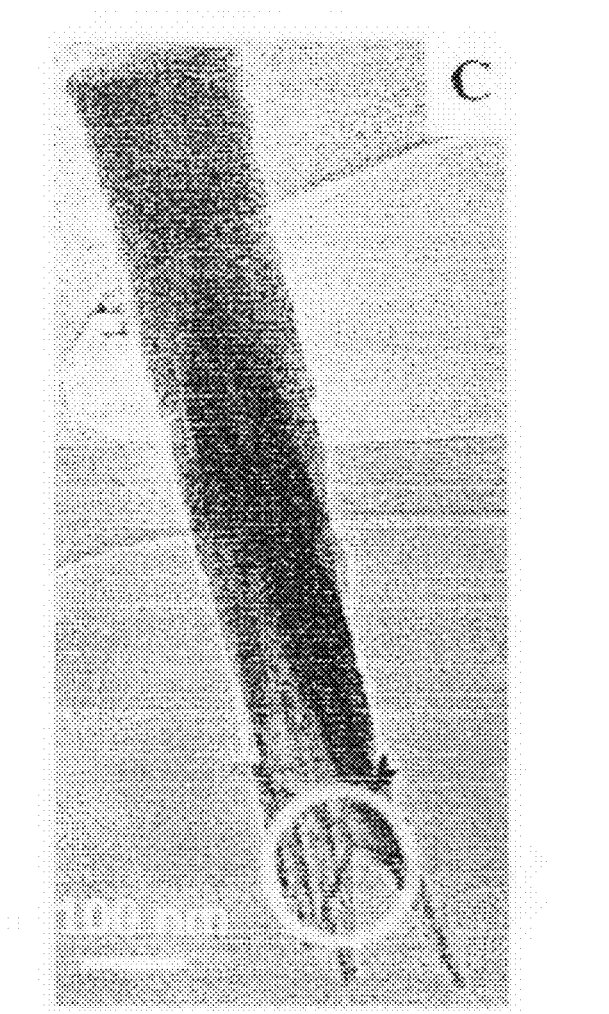
FIG. 3C. TEM image of a single half of a sheaf-like nanostructure bundle.
Figure 3D:
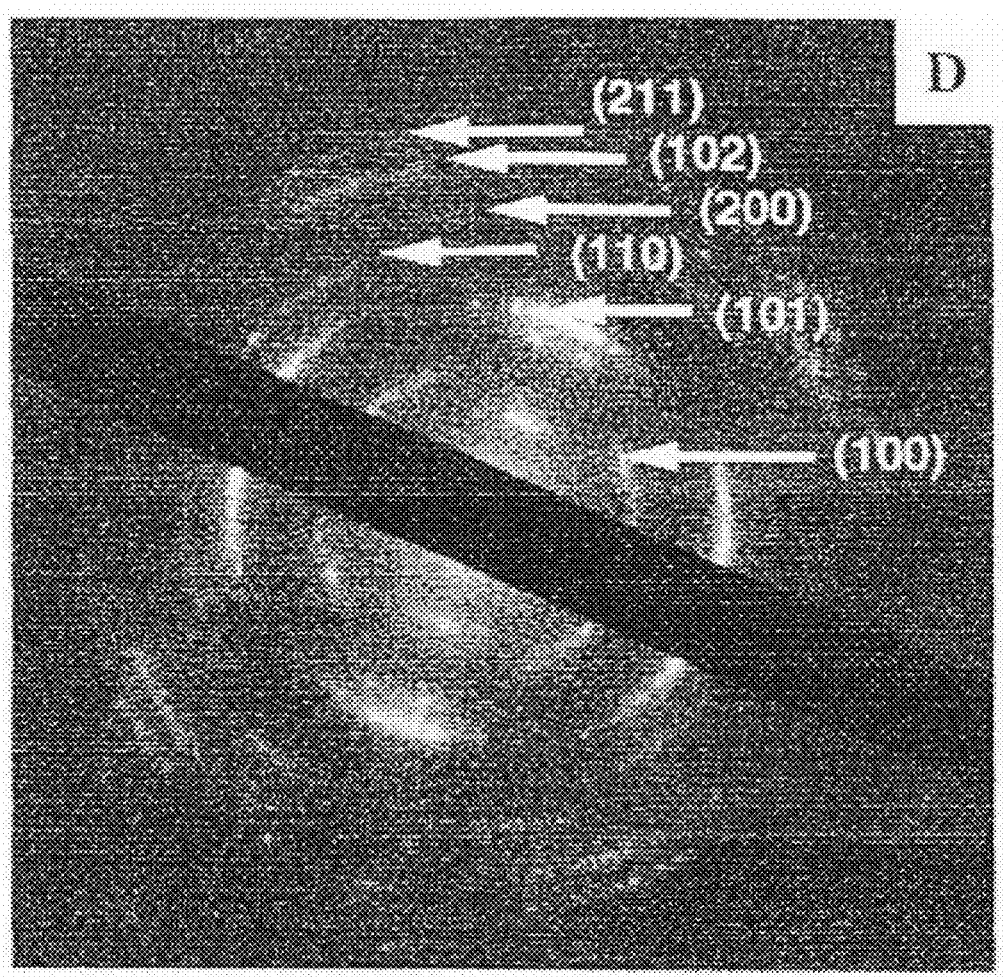
FIG. 3D. SAED pattern of a single half of a sheaf-like nanostructure bundle corresponding with the TEM image of FIG. 3C.
Figure 3E:
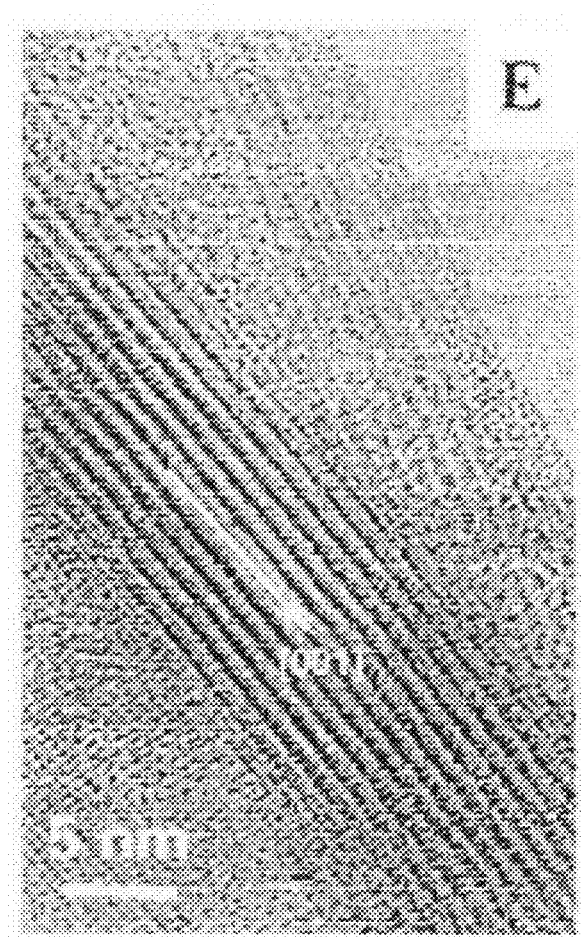
FIG. 3E. HRTEM image of a representative section at the tip of a sheaf-like bundle, highlighted by a white circle in FIG. 2C.
Figure 3F:
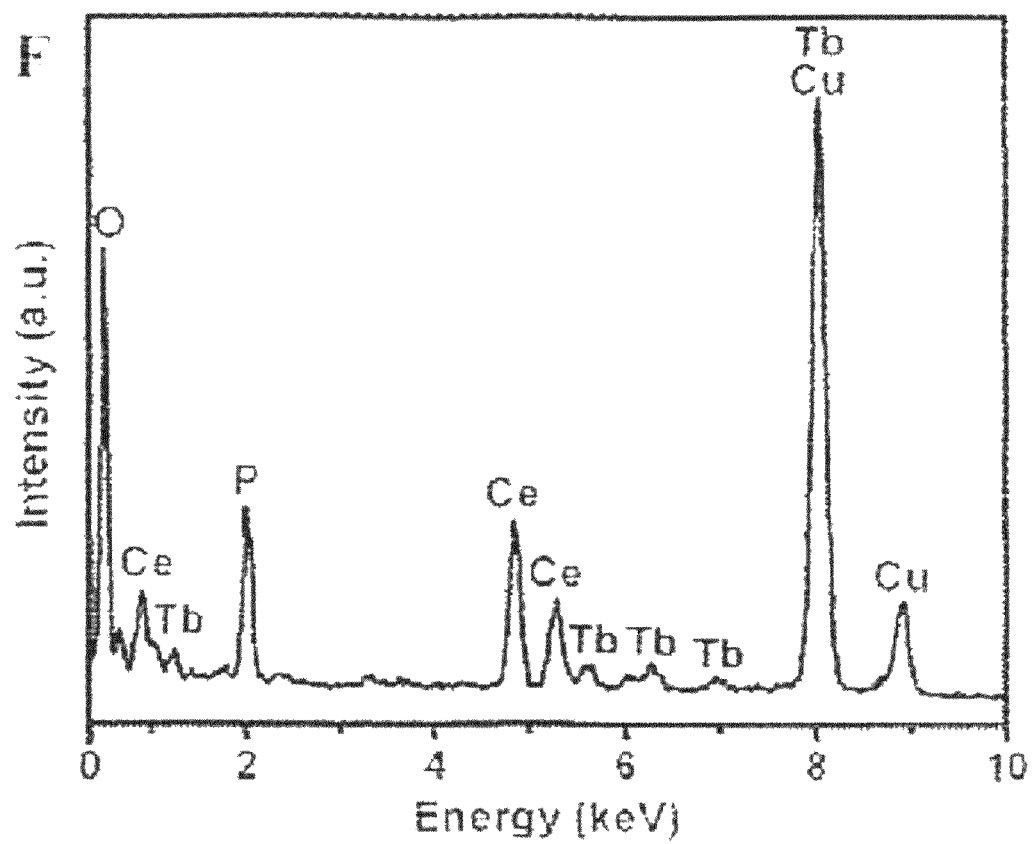
FIG. 3F. EDS spectrum of as-prepared Tb-doped $CePO_4$ sheaf-like nanostructures. The Cu peaks originate from the TEM grid.

Although symmetric hay stack-like aggregates, composed of sheaf-like bundles projecting out at both ends, were often obtained, asymmetric, truncated structures consisting of sheaf-like bundles protruding from only one end formed the majority of as-prepared products isolated from within the template membrane pores. For example, FIG. 3C shows a representative, asymmetric, truncated sheaf-like bundle. The associated SAED pattern is consistent with that of pure $CePO_4$ crystals pertaining to a hexagonal structure, as indexed in FIG. 3D. The slightly diffuse, textured ring pattern is consistent with a sheaf-like bundle of nanoscale bristles partially aligned along the common axis. HRTEM analysis (FIG. 3E) of the end of an individual sheaf-like bundle nanostructure indicates that each constituent bristle is single-crystalline without any visible defects and dislocations, although their total absence in the sample cannot be ruled out. The calculated interplanar distance is about 0.63 nm, corresponding to the (100) crystal plane of hexagonal $CePO_4$ crystals. This observation suggests that the nanoscale bristles are structurally uniform single crystals with a preferential growth direction of [001], e.g. identical to the c-axis of the ultrathin nanowires isolated from solution. The chemical signatures obtained from EDS spectra (FIG. 3F) are identical within experimental accuracy, and only Tb, Ce, P, and O elements were observed, as expected. The Cu signal arose from the TEM grid.

Without wanting to be held to a mechanism, it is theorized that a splitting growth mechanism may account for the observed morphological motifs. In particular, crystal splitting is associated with fast crystal growth and depends strongly on the oversaturation of the solution (Shen et al., *Angew. Chem. Int. Ed.* 2007, 46, 7659-7663). It has been suggested that splitting is only possible if the oversaturation exceeds a certain critical level, unique to each material (Tang et al., *Nano Lett.* 2006, 6, 2701-2706). Factors known to cause crystal splitting include mechanical splitting (i.e. when extra molecules appear in some layers of its crystallographic network) and chemical splitting (i.e. when certain ions are present in the parent solution). Because faster growth is also expected to result in a higher density of defects in the resulting structures, the observation of crystal splitting in bundles of $Bi_2S_3$ nanorods led one group (Stavila et al., *Chem. Mater.* 2009, 21, 5456-5465) to postulate that the strain field caused by the presence of these linear and planar defects as well as atomic distortions, created during the growth process, is a key contributor to this phenomenon.

According to a plausible crystal splitting scenario, new surface area is created each time the crystal splits and the balance between bulk and surface energies determines the particular crystal size obtainable. Therefore, under the ambient, low-temperature conditions herein, there is an initial formation of only a few nuclei just after supersaturation followed by subsequent fast growth to a situation of metastability wherein crystals can grow beyond this size. It is then thermodynamically favorable for the large crystal to split, partly because of the strong adhesion of an additive, such as the $H^+$ highly prevalent in an acidic environment, to the newly created surface (Tang et al., *Nano Lett.* 2006, 6, 2701-2706).

Hence, by this mechanism, a single nanowire can essentially branch into a sheaf (Kelly et al., *Nano Lett.* 2007, 7, 2920-2925).

The growth mechanism involves a double-diffusion crystallization process, set in a U-tube which enables the continuous flow of precursor ions into spatially confined membrane pores (Peters et al., *J. Chem. Soc., Dalton Trans.* 2001, 3585-3592; Park et al., *J. Mater. Chem.* 2004, 14, 2291-2296; Park et al., *Adv. Mater.* 2004, 14, 1167-1169). One of the two half cells was filled with a 0.01 M $NaH_2PO_4$ solution, and the other half cell contained a solution by mixing 0.05 M $CeCl_3$ solution together with $Tb(NO_3)_3$ up to a final molar concentration of 10.0%, so as to generate desired Tb-doped $CePO_4$ nanostructures. In order to prevent overly rapid mixing, the solutions are separated by a polycarbonate membrane that slows down diffusion and the rate of crystallization. However, when the two solutions do meet, precipitation occurs, depleting the availability of ions in the local environment of the growing crystal within the template. The nucleation rate is primarily dictated by the supersaturation of the solution. Further growth of the nanostructures is limited by diffusion of ions in this localized region.

Without wanting to be held to a mechanism, it is believed that the initially formed ultrathin nanowires have a strong tendency to aggregate as larger ones and that the acidic medium was conducive to the self-assembly and subsequent crystal splitting of these as-formed bundles into sheaf-like patterns that propagate along the c-direction of elongation. This hypothesis is supported by that the constituent bristles associated with the sheaf-like structure not only possess the same diameter range but also appear to grow along the [001] direction, precisely analogous to the ultrathin Tb-doped $CePO_4$ nanowires collected from the solution. The constituent bristles of the sheaths continually grow at a rate controlled by incident precursor ion diffusion, until they protrude externally from the template pores into solution. It has been previously observed for metals, that growing, elongating nanowires can attain sizes, that are significantly greater than the limited ~6 μm length of the template pore channels themselves (Sharabani et al., *Nano Lett.* 2008, 8, 1169-1173). Essentially, the nanowires then randomly break, perhaps due to mechanical fracturing as a result of the presence of defects, (Brambilla et al., *Nano Lett.* 2009, 9, 831-835) leading to the isolation of >10 μm long ultrathin nanowires in solution and remnant sheaf-like structures within the template pores themselves.

Figure 4:
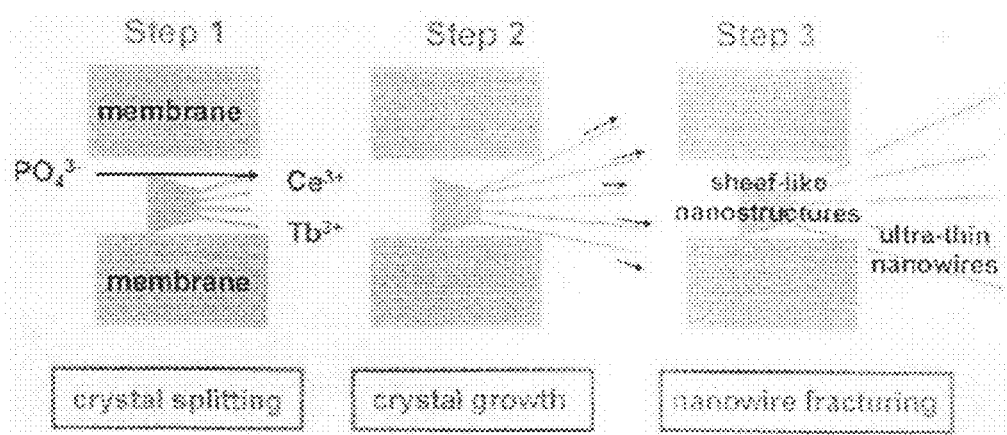
FIG. 4. Proposed schematic to account for observed morphologies of ultrathin nanowires and sheaf-like bundles. Step 1: Crystal splitting. Fast growth leads to a metastable state, wherein it becomes thermodynamically favorable for a large crystal to split. Step 2: Selective growth of constituent bristles of sheaf-like bundles along the c-axis at a rate controlled by precursor ion diffusion. Step 3: Fragmentation (perhaps due to mechanical instability) of nanowires into ultrathin products that are subsequently isolated in solution.

A summary of the formation mechanism is highlighted in FIG. 4. In support of this mechanistic interpretation, additional reactions were conducted. For example, even after a couple of minutes of reagent mixing between the two precursor solutions localized in the two half-arms of the U-shaped tube, the effects of crystal splitting were observed in the product morphology, accompanied by a visual occlusion of the reaction solution medium. Also, when any additional sonication step that might disperse the fractured nanostructures was purposely omitted, the presence in solution, external to the template, of isolated clusters of nanowire agglomerates was noted, which have retained their initial bundle-like motif. This result, which is compatible with the $3^{rd}$ step of the protocol, further confirms the plausibility of crystal splitting formation mechanism.

To verify that the pores of the membrane are essential for the directed formation of Tb-doped $CePO_4$ nanostructures, reagent solutions were directly mixed in the absence of a polycarbonate membrane. Neither sheaf-like nanostructures nor ultrathin nanowires were evidently formed. In fact, direct mixing yielded a supersaturated medium and led to the formation of a large number of amorphous, irregular-looking particles. As an experimental observation worthy of note, far fewer nanowires were isolated from the half-cell containing the $NaH_2PO_4$ solution, suggesting that the diffusion rate of $PO_4^{3-}$ anionic groups was likely faster than that of either $Ce^{3+}$ or $Tb^{3+}$ cations under ambient, acidic reaction conditions. Moreover, after continuous extraction of suspended ultrathin nanowires, it was noted that a continuous addition of precursor solutions into the U-tube cells, still separated by a template membrane containing chemically active sheaf-like bundles of nanostructures, resulted in additional, unimpeded production of high-quality, single-crystalline ultrathin nanowires. The data therefore strongly imply an ambient, green methodology for the large-scale and facile production of lanthanide-doped cerium phosphate nanowires.

Figure 5:
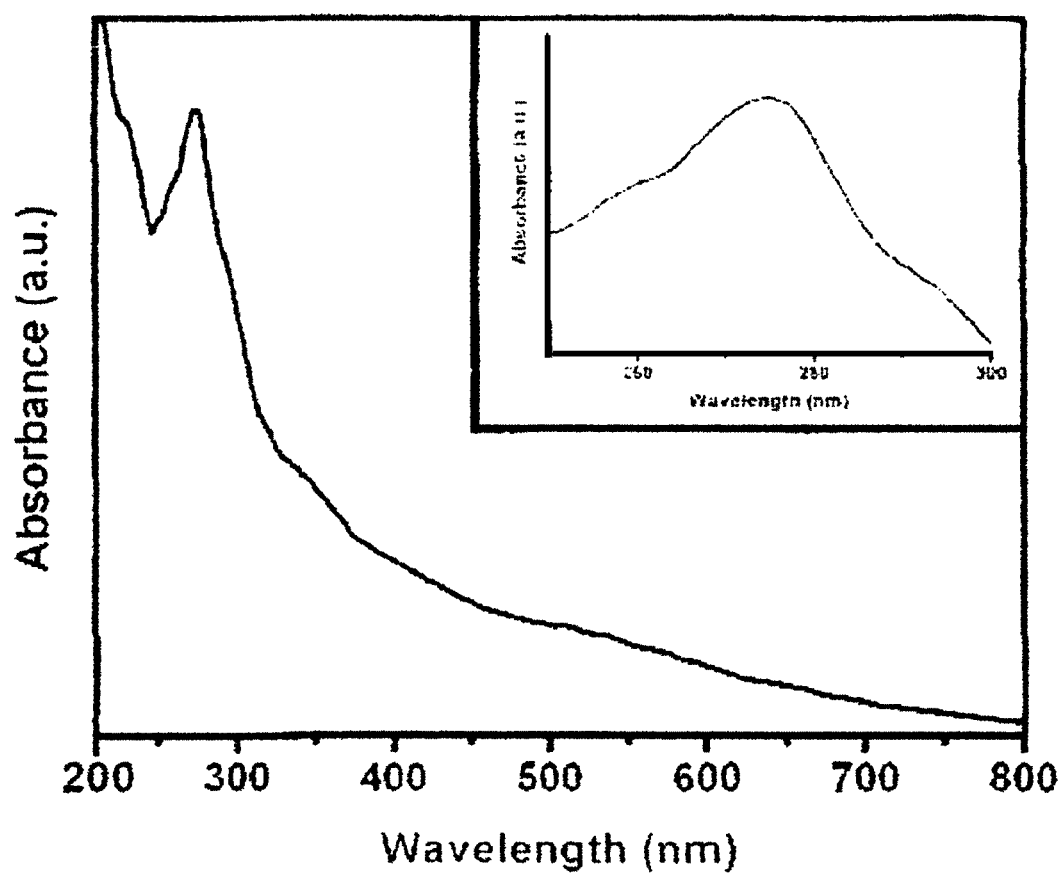
FIG. 5. UV-visible spectrum of as-prepared Tb-doped $CePO_4$ nanowires. Expanded region between 220 and 300 nm is shown as an inset.

UV-visible Spectroscopy and Photoluminescent Activity. The optical properties of the as-prepared ultrathin Tb-doped $CePO_4$ nanowires have been investigated. Cerium-based compounds, such as $CeO_2$, $CeP_2O_7$ and $CePO_4$, are known to have strong absorption for the ultraviolet and have been considered for applications such as tunable sunscreen materials (Imanaka et al., *Chem. Lett.* 2003, 32, 400-401; Imanaka et al., *Chem. Mater.* 2003, 15, 2289-2291). FIG. 5 highlights the UV-visible absorption spectra of thin nanowires collected from solution. A magnified view of the region between 220 and 300 nm is shown as an inset, consisting of two major peaks located at 258 and 275 nm coupled with small shoulder-like substructure: These bands are overlapping as the excited state is strongly split by the crystal field (Li et al., *Angew. Chem., Int. Ed.* 2007, 46, 3486-3489). Moreover, the results are consistent with reported data for transitions from the ground state $^2F_{5/2}$ ($4f^1$) of $Ce^{3+}$ to the five crystal field split levels of the $Ce^{3+2}D(5d^1)$ excited states (namely $^2D_{5/2}$ and $^2D_{3/2}$), suggesting that useful optical properties were retained in the nanostructured materials (Xing et al., *J. Phys. Chem. B* 2006, 110, 1111-1113). Differences in the spectral behavior between the $CePO_4$ bulk and their nanoscale analogues have often been attributed to the presence of a higher degree of disorder and lattice distortion in the nanowires and the fact that there is a lower crystal field symmetry in these nanowires as compared with the bulk (Fang et al., *J. Am. Chem. Soc.* 2003, 125, 16025-16034).

The excitation spectrum ($\lambda_{em}$=542 nm) of the as-prepared Tb-doped nanowires consists of an intense, broad feature from ~250 to 320 nm with a maximum at 275 nm. Prior reports (Chen et al., *J. Phys. Chem. C* 2008, 112, 20217-20221; Yu et al., *Solid State Commun.* 2005, 134, 753-757; Yu et al., *J. Phys. Chem. B* 2005, 109, 11450-11455; Buchold et al., *Adv. Funct. Mater.* 2008, 18, 1002-1011) have ascribed these bands to allowed f-d transitions from the $^2F_{5/2}$ ground state of $Ce^{3+}$ to different crystal-field components of the 5d level, such as the $^2D_{3/2}$ state.

Figure 6:
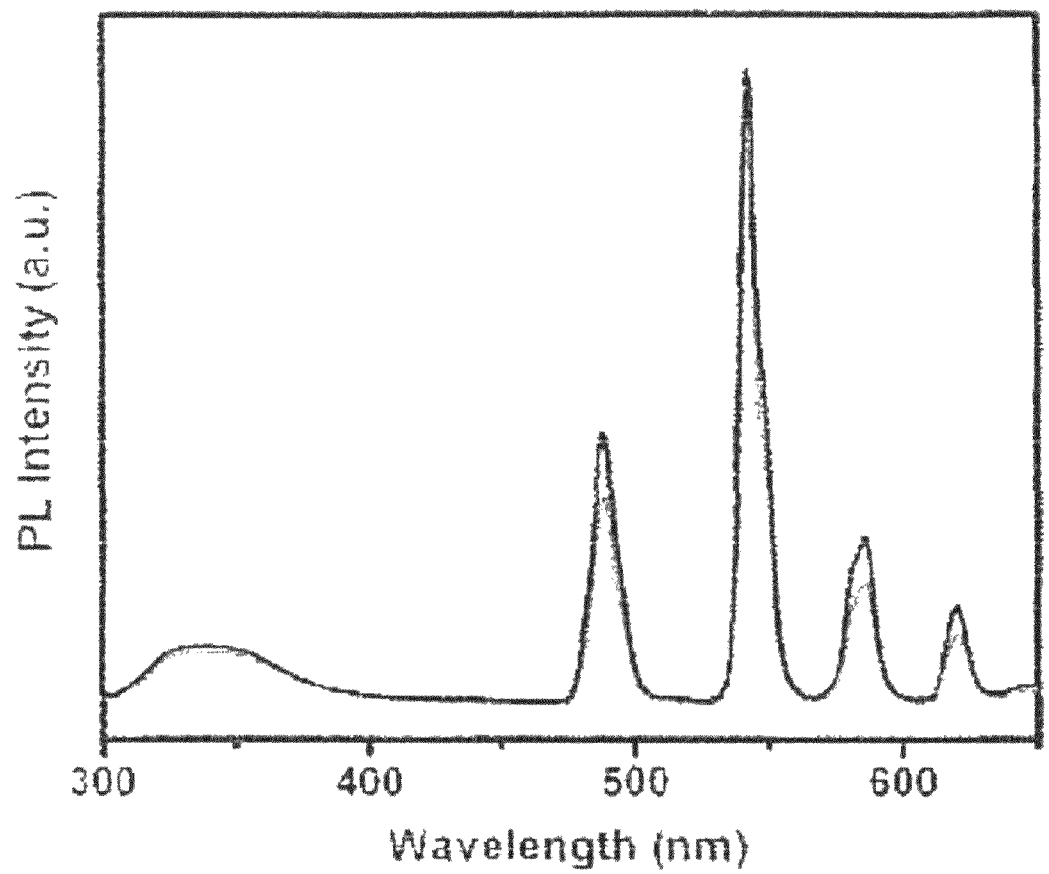
FIG. 6. Photoluminescence spectra, obtained upon excitation at 256 nm at room temperature, of as-prepared Tb-doped $CePO_4$ nanowires before bold lined curve and after thin lined curve five successive redox cycles.

The black curve in FIG. 6 highlights the room-temperature photoluminescent emission spectrum of Tb-doped $CePO_4$ nanowires in water upon excitation at 256 nm (where $Tb^{3+}$ absorption is minimal) at room temperature. The actual doping concentration and inherent density of lanthanide ions are optically significant (Yu et al., *Solid State Commun.* 2005, 134, 753-757) in terms of governing measured emission intensities (Chen et al., *J. Phys. Chem. C* 2008, 112, 20217-20221). However, corresponding effects due to particle sizes on the emission signal are expected to be weak, since transitions of the well-shielded f electrons are mainly affected by the local symmetry of the crystal site (Riwotzki et al., *Angew. Chem. Int. Ed* 2001, 40, 573-576). Indeed, the data consists of four well-resolved peaks between 450 and 650 nm, corresponding to the $^5D_4$-$^7F_J$(J=6, 5, 4, 3) transitions of $Tb^{3+}$ ions.

Specifically, these four peaks positioned at 488, 542, 586, and 620 nm can be ascribed to $Tb^{3+}$ emission resulting from $^5D_4$-$^7F_6$, $^5D_4$-$^7F_5$, $^5D_4$-$^7F_4$, and $^5D_4$-$^7F_3$ relaxations, respectively (Li et al., *Angew. Chem., Int. Ed* 2007, 46, 3486-3489; Rambabu et al., *Mater. Chem. Phys.* 2003, 78, 160-169; Fu et al., *Solid State Sci.* 2008, 10, 1062-1067; Kompe et al., *Angew. Chem. Int. Ed* 2003, 42, 5513-5516). The most intensive peak is located at 542 nm, consistent with the observed bright green luminescence of these samples.

The broad band between 300 and 400 nm has been previously ascribed to 5d-4f transitions of $Ce^{3+}$. Owing to the relatively high concentration of $Ce^{3+}$ in the nanowires, the excited state of $Ce^{3+}$ is not completely quenched by energy transfer to $Tb^{3+}$ (Chen et al., *J. Phys. Chem. C* 2008, 112, 20217-20221; Zhu et al., *Nanotechnology* 2006, 17, 4217-4222). In fact, the nature of the observed photoluminescence is dependent upon the probability of energy transfer through the host cerium lattice (governed by factors such as electric dipole-dipole interaction and reabsorption of emission) as well as the probability of energy transfer from the lattice to the $Tb^{3+}$ 'activator' (Blasse et al. *J. Chem. Phys.* 1969, 51, 3252-3254; Bourcet et al., *J. Chem. Phys.* 1974, 60, 34-39). The intrinsic emission of $Ce^{3+}$, associated with two transitions from the lowest component of the $^2D$ state to the spin-orbit components of the ground state, $^2F_{7/2}$ and $^2F_{5/2}$, (Riwotzki et al., *Angew. Chem. Int. Ed.* 2001, 40, 573-576) is a broad band. By contrast, the absorption of $Tb^{3+}$ consists of narrow lines (Shionoya et al., *Appl. Phys. Lett.* 1965, 6, 118-120). The expected energy transfer process between $Ce^{3+}$ and $Tb^{3+}$ is schematically depicted in FIG. S8, wherein energy transfer takes place from the $^5D_{3/2}$ state of the $Ce^{3+}$ 'sensitizer' to the acceptor states of $Tb^{3+}$, which decay non-radiatively to the $^5D_4$ and $^5D_3$ states followed by a radiative decay process to lower levels of $^7F_J$ (J=0-6) (Li et al., *Angew. Chem., Int. Ed* 2007, 46, 3486-3489).

However, efficient energy transfer between cerium and terbium is possible only between nearest neighbors in the crystal lattice and when there is optimal spectral overlap (Jose et al., *Opt. Mater.* 2004, 24, 651-659). Therefore, if there is radiative transfer, some narrow dips at the location of $Tb^{3+}$ absorption lines would appear to be associated with an emission intensity decrease but the depression of the entire cerium emission spectrum would not occur. This incomplete energy transfer from $Ce^{3+}$ to $Tb^{3+}$ has been observed for bulk analogues as well as for other Ce-based matrices (Shionoya et al., *Appl. Phys. Lett.* 1965, 6, 118-120; Blasse et al. *J. Chem. Phys.* 1969, 51, 3252-3254; Zhang et al., *J. Phys. Chem. C* 2008, 112, 10083-10088).

Photoluminescence switching behavior has been previously observed in these systems, (Li et al., *Angew. Chem., Int. Ed* 2007, 46, 3486-3489; Chen et al., *J. Phys. Chem. C* 2008, 112, 20217-20221; Zhang et al., *J. Phys. Chem. C* 2008, 112, 10083-10088) related to dramatic changes in the emission intensity of $Tb^{3+}$, upon oxidation and reduction processes. Specifically, upon addition of $KMnO_4$ to the as-prepared colloidal dispersion of Tb-doped $CePO_4$ nanowires, $Ce^{3+}$ was oxidized to $Ce^{4+}$, essentially suppressing the observed emission entirely. Subsequent reduction of $Ce^{4+}$ to $Ce^{3+}$ through the addition of ascorbic acid ($C_6H_8O_6$) to the oxidized nanowire solution effectively restored the observed luminescence to its original profile.

As shown in FIG. 6, the switching process is reversible. That is, the photoluminescence spectra of as-prepared Tb-doped $CePO_4$ nanowires and of samples taken after five successive redox cycles are shown in which the luminescence of these nanostructures was repeatedly quenched ('off' state) by oxidation with $KMnO_4$ followed by its recovery ('on' state) by reduction with ascorbic acid. The emission profiles are essentially identical with only a slight degradation in luminescence intensity with no apparent change in nanowire morphology. In fact, the ratio of luminescence intensities taken of the nanowire samples before and immediately after five successive $KMnO_4$/ascorbic acid redox cycles was as much as 95% at the 542 nm emission peak. These results demonstrate that the as-prepared ultrathin Tb-doped $CePO_4$ nanowires are robust and the reproducible change in luminescence signal can theoretically be used to as a sensitive and rapid indicator of the redox behavior of their surrounding environments. Moreover, owing to their reported low toxicity (Li et al., *Angew. Chem., Int. Ed.* 2007, 46, 3486-3489) and reasonable dispersibility in cell culture medium (up to as much as 0.5 mg/mL for a period of 2 days), these nanostructures are potentially viable candidates for biological labels and probes.

Biocompatibility and Potential for Bioimaging. Generally, the cellular permeability and cytotoxicity characteristics of fluorescent nanomaterials are critical to their applications as luminescent biological labels. It has already been established that inorganic fluorescent lanthanide (europium and terbium) orthophosphate (e.g. $EuPO_4.H_2O$ and $TbPO_4.H_2O$) nanorods, synthesized, by a microwave technique, can behave as biolabels and can be internalized into either human umbilical vein endothelial cells, 786-O cells, or renal carcinoma cells, though the exact mechanism for their internalization remained unclear (Patra et al., *J. Nanobiotechnol.* 2006, 4, 1-15, Patra et al., *Clin. Chem.* 2007, 53, 2029-2031). Hence, to confirm the potential applicability of the ultrathin green luminescent Tb-doped $CePO_4$ nanowires of the present invention in a biological system, analogous experiments were conducted using HeLa cells measuring 12 to 20 μm in diameter. To facilitate processing, prior to cellular incubation, the as-prepared thin, long nanowires were sonicated for ~1 hour in order to generate noticeably shorter structures (FIG. S10), measuring 3.2±2 μm in length.

As a control experiment, HeLa cells alone showed negligible background fluorescence under two-photon excitation. Nonetheless, upon incubation, incorporation of cut, as-prepared Tb-doped $CePO_4$ nanowires into HeLa cells was confirmed by confocal fluorescence microscopy. Specifically, after incubation with 2 mg/mL of Tb-doped $CePO_4$ nanowires for 2 h at 37° C., an intense intracellular luminescence was observed. These inorganic phosphate nanowires clearly retained their intrinsic fluorescent properties upon cellular internalization. Moreover, the corresponding bright-field measurements taken after treatment with the nanowires confirmed that the cells were viable throughout the imaging experiments and that there were no evident regions of cell death. Overlays of both confocal luminescence and bright-field images further demonstrated that the observed luminescence was noticeable throughout the entire intracellular region, thereby strongly suggesting that the nanowires were internalized into the cells themselves as opposed to merely staining the external membrane surface (Hu et al., *Chem. Mater.* 2008, 20, 7003-7009).

To confirm the spatial localization of nanowires within a typical cell, a series of Z-stack images of the cell (e.g. top to bottom) at 1 μm 'slice' intervals of an individual HeLa cell stained with Tb-doped $CePO_4$ nanowires was obtained. Data associated with the middle, central slice, corresponding to orthogonal xy, yz, and xz planes, respectively, are shown. Because these three planes share a common focal center within the cell itself and moreover, as these intimately interconnected planes evidently all demonstrate green fluorescence simultaneously, it can reasonably be concluded that the fluorescently doped lanthanide nanowires are localized within the interior environment of the HeLa cells themselves.

A dramatic decrease in the fluorescence intensity in data taken after identical cellular incubation with the as-prepared Tb-doped CePO$_4$ nanowires at the same concentrations was noted, but at a noticeably lower temperature (i.e. 4° C.), as compared with that observed in cells treated with nanowires at 37° C. The overlap image (FIG. 7D) suggests that there was little if any nanowire incorporation.

Overall, these data are consistent with prior work on oxidized single-walled carbon nanotubes (SWNTs), wherein their internalization into HeLa cells involved a temperature-dependent diffusion process akin to a "pierce-through" mechanism (Chen et al., *J. Am. Chem. Soc.* 2008, 130, 16778-16785). That is, these SWNTs tended to act as nanoneedles that could pierce through cell membranes, thereby allowing for their diffusion into cells (Kostarelos et al., *Nature Nanotechnology* 2007, 2, 108-113). It is believed that in the lanthanide nanowires of the present invention, receptor-mediated endocytosis was involved in the observed cellular internalization.

The present experiments were conducted in cell culture media. It has been recently reported that serum proteins from biological media, such as bovine serum albumin (BSA), can non-specifically coat the surfaces of gold nanorods, leading to all nanorod samples bearing the same effective charge, regardless of their initial surface charge (Alkilany et al., *Small* 2009, 5, 701-708; Chithrani et al., *Nano Lett.* 2006, 6, 662-668). In that system, it was proposed that externally adsorbed BSA facilitated the uptake of nanorods into human cancer cells, such as either HeLa or HT-29, via receptor-mediated endocytosis arising from cellular recognition of these proteins. It is very plausible to imagine an analogous scenario herein, especially since BSA has been previously noted to be able to nonspecifically adsorb onto a diverse range of different surfaces, functionalized or not (Silin et al., *J. Coll. Interf. Sci.* 1997, 185, 94-103; Rezwan et al., *Langmuir* 2004, 20, 10055-10061).

The present results confirm that as-prepared Tb-doped CePO$_4$ nanowires can be used as fluorescent labels for biological imaging. The HeLa cells were also incubated with different concentrations (ranging from 0.1 to 0.5 mg/mL) of as-prepared Tb-doped CePO$_4$ nanowires in order to test their inherent sensitivity as luminescent probes. An analysis of the corresponding CFM intensities, proportional to the number of doped phosphate nanowires internalized by the HeLa cells, demonstrates an increase in the measured fluorescence, with increasing nanowire concentrations and cellular incubation periods. The data show that even nanowire concentrations as low as 0.1 mg/mL and incubation times as short as 2 h can yield sufficient nanowire integration into HeLa cells so as to generate sufficiently strong fluorescence for bioimaging purposes.

Furthermore, Tb-doped CePO$_4$ nanowires, subjected to repeated redox cycles, were also incubated with HeLa cells. The degree of cellular uptake was analogously to confirmed by CFM data. Specifically, 'oxidized' nanowires did not evince any fluorescence within cells, whereas cells treated with 'reduced' nanowires demonstrated a measurable degree of fluorescence. Quantitatively, as compared with as-prepared nanowires, there was a small decrease (7% to 13%) in the fluorescence intensity measured in cells. This value was comparable in magnitude to the decrease observed in pure nanowire suspensions, as measured by PL spectroscopy (FIG. 6).

Moreover, to verify whether these ultrathin Tb-doped CePO$_4$ nanowires are biologically nontoxic and biocompatible, cytotoxicity studies of HeLa cells were performed, based on the reduction activity of methyl thiazolyl tetrazolium (MTT), based on previous analogous work (Hu et al., *Chem. Mater.* 2008, 20, 7003-7009). The viability of untreated cells was assumed to be 100%. Upon incubation of HeLa cells with a 0.1 mg/mL solution of Tb-doped CePO$_4$ nanowires, it was noted that fewer than 15% of the cells died after a 48 h exposure. When the concentration of nanowires was increased to 0.5 mg/mL, the observed cell viability still remained above 80%, again after 48 h of exposure. Therefore, these data strongly suggested that ultrathin Tb-doped CePO$_4$ nanowires can be considered to possess reasonably low cytotoxicity, which is in agreement with previous reports that rare-earth-based nanophosphors maintain reasonable chemical stability and generally low toxicity, which are essential for legitimate bioimaging applications (Hu et al., *Chem. Mater.* 2008, 20, 7003-7009; Palmer et al., *Environ. Res.* 1987, 43, 142-156).

Further Observations

The present invention includes a simple, effective, and versatile template-directed method for the successful large-scale preparation of Tb-doped CePO$_4$ nanowires possessing very high aspect ratio, under ambient room temperature conditions. Sheaf-like bundles of ultrathin 1D nanostructures may initially form through a crystal splitting growth mechanism, followed by continuous growth out of template membrane pore channels, until they finally fracture in solution. This new synthetic approach is important not only because it involves a number of intriguing fundamental steps, but also because this environmentally benign route can be readily extended to the synthesis of other kinds of rare-earth phosphate nanomaterials either with or without dopants. The resulting Tb-doped CePO$_4$ nanowires displayed a redox-switchable green photoluminescence that was subsequently exploited for biological labeling purposes. Moreover, it was noted that the nanostructures not only were biocompatible with cells but also were relatively nontoxic over reasonable time periods and concentrations, of significance for applications in biomedical diagnostics and analyses Although preferred embodiments of the present invention have been described herein with reference to the accompanying drawings, it is to be understood that the invention is not limited to those precise embodiments and that various other changes and modifications may be effected herein by one skilled in the art without departing from the scope or spirit of the invention, and that it is intended to claim all such changes and modifications that fall within the scope of the invention.

The invention claimed is:

1. A method of producing a single crystalline metal sulfide nanostructure, the method comprising:
   providing a metal precursor solution and providing a sulfur precursor solution;
   placing a porous membrane between the metal precursor solution and the sulfur precursor solution, wherein metal cations of the metal precursor solution and sulfur ions of the sulfur precursor solution react, thereby producing a single crystalline metal sulfide nanostructure, wherein the metal is a transitional metal or a Group IV metal,
   and wherein the nanostructure is a one dimensional nanostructure.

2. A method of claim 1 wherein the metal is selected from the group consisting of copper, lead, cadmium, iron, manganese, cobalt, nickel, zinc, magnesium, tin, germanium, or mixtures thereof.

3. A method of claim 1 wherein the metal is selected from the group consisting of copper, lead, and cadmium.

4. The method of claim 1 wherein metal cations and sulfide ions predominantly nucleate to form metal sulfides within confines of pores of the porous membrane.

5. The method of claim 1 wherein the metal cations and sulfide ions predominantly nucleate at the surfaces of pore walls of the porous membrane.

6. A method of producing a single crystalline cadmium sulfide nanostructure, the method comprising:
   providing a cadmium precursor solution, and providing a sulfur precursor solution;
   placing a porous membrane between the cadmium precursor solution and the sulfur precursor solution, wherein cadmium cations of the cadmium precursor solution and sulfur ions of the sulfur precursor solution react, thereby producing a single crystalline cadmium sulfide nanostructure,
   wherein the method takes place at about 70° C. to about 85° C., and wherein the nanostructure produced is a cactus-like nanostructure.

7. A crystalline nanostructure comprising hexagonal würtzite cactus-like cadmium sulfide nanostructures, produced by a method comprising:
   providing a metal precursor solution and providing a sulfur precursor solution;
   placing a porous membrane between the metal precursor solution and the sulfur precursor solution, wherein metal cations of the metal precursor solution and sulfur ions of the sulfur precursor solution react, thereby producing a single crystalline metal sulfide nanostructure, wherein the metal is a transitional metal or a Group IV metal.

8. A method of producing an array of single crystalline metal sulfide nanostructures, the method comprising:
   providing a metal precursor solution and providing a sulfur precursor solution;
   placing a porous membrane between the metal precursor solution and the sulfur precursor solution, wherein metal cations of the metal precursor solution and sulfur ions of the sulfur precursor solution react, thereby producing a single crystalline metal sulfide nanostructure, wherein the metal is a transitional metal or a Group IV metal,
   wherein the nanostructure is an array of one dimensional nanostructures.

* * * * *